US012799064B2

(12) United States Patent
Shuto et al.

(10) Patent No.: US 12,799,064 B2
(45) Date of Patent: Nov. 17, 2026

(54) STABLE EQUIVALENT OF RESOLVIN E2

(71) Applicant: NATIONAL UNIVERSITY CORPORATION HOKKAIDO UNIVERSITY, Sapporo (JP)

(72) Inventors: Satoshi Shuto, Sapporo (JP); Tadashi Matsuda, Sapporo (JP); Ryuta Muromoto, Sapporo (JP); Hayato Fukuda, Sapporo (JP)

(73) Assignee: National University Corporation Hokkaido University, Sapporo (JP)

( * ) Notice: Subject to any disclaimer, the term of this patent is extended or adjusted under 35 U.S.C. 154(b) by 996 days.

(21) Appl. No.: 17/799,953

(22) PCT Filed: Feb. 18, 2021

(86) PCT No.: PCT/JP2021/006102
§ 371 (c)(1),
(2) Date: Aug. 16, 2022

(87) PCT Pub. No.: WO2021/166998
PCT Pub. Date: Aug. 26, 2021

(65) Prior Publication Data

US 2023/0099067 A1 Mar. 30, 2023

(30) Foreign Application Priority Data

Feb. 18, 2020 (JP) ................................ 2020-025666

(51) Int. Cl.
*C07C 57/30* (2006.01)

(52) U.S. Cl.
CPC .................................... *C07C 57/30* (2013.01)

(58) Field of Classification Search
CPC ....... C07C 57/30; C07C 59/48; C07D 309/30; A61P 29/00
See application file for complete search history.

(56) References Cited

U.S. PATENT DOCUMENTS 4,032,656 A 6/1977 Groves et al.

FOREIGN PATENT DOCUMENTS

| | | | |
|---|---|---|---|
| EP | 207599 A | * | 1/1987 |
| JP | 2007-504134 A | | 3/2007 |

OTHER PUBLICATIONS

Notice of Allowance from JP Application No. 2022-501964 dated Jan. 10, 2023.
Serhan and Petasis, "Resolvins and Protectins in Inflammation Resolution," Chemical Reviews, 2011, vol. 111(10), p. 5922-5943.
Fukuda et al., "Design and Synthesis of Cyclopropane Congeners of Resolvin E2, an Endogenous Proresolving Lipid Mediator, as Its Stable Equivalents," Organic Letters, 2016, vol. 18(24), p. 6224-6227.
Deyama et al., "Resolvin E1/E2 ameliorate lipopolysaccharide-induced depression-like behaviors via ChemR23," Psychopharmacology, 2018, vol. 235, p. 329-336.
Ningzhang Zhou et al., "H-Shaped OPE/OPV Oligomers: A New Member of 2D-Conjugated Fluorophore Cores," Organic Letters, 2008, vol. 10(14), p. 3001-3004.
Jean-Martial L'Helgoual'ch et al., "Deprotonative cadmation of functionalized aromatics," Chem. Commun., 2008, 5375-5377.
Gotz, K., Liermann et al., "Structure elucidation of hypocreolide A by enantioselective total synthesis," Org. Biomol. Chem., 2010, 8, 2123-2130.
Corey, E. J. et al., "An Enantioselective Synthetic Route to Atractyligenin Using the Oxazaborolidine-Catalyzed Reduction of B-Silyl- or B-Stannyl-Substituted a,B-Enones as a Key Step," J. Am. Chem. Soc, 1997, 119, 11769-11776.
Boer, R. E. et al., "Total Synthesis and Biological Activity of the Arachidonic Acid Metabolite Hemiketal E2," Organic Letters, 2018, 20, p. 4020-4022.
Sun, Y. et al., "Anti-inflammatory and pro-resolving properties of benzo-lipoxin A4 analogs," Prostaglandins, Leukotrienes and Essential Fatty Acids, 2009, 81(5-6), p. 357-366.

(Continued)

*Primary Examiner* — Rayna Rodriguez
(74) *Attorney, Agent, or Firm* — Calfee, Halter & Griswold LLP

(57) ABSTRACT

The present invention provides a compound represented by General Formula (1) or (1') [in the formula, $R^1$ and $R^2$ each independently represents a hydrogen atom or a hydroxy group; $R^3$ represents an alkyl group having 1 to 6 carbon atoms; $R^4$ represents a halogen atom or an alkyl group; m indicates the number of $R^4$ and represents an integer of 0 to 4; in a case where m is 2 or more, a plurality of $R^4$'s may be the same or different from each other; n represents an integer of 1 to 6; and n' represents an integer of 1 to 4] and a neutrophil infiltration suppressor containing the compound as an active ingredient.

(1)

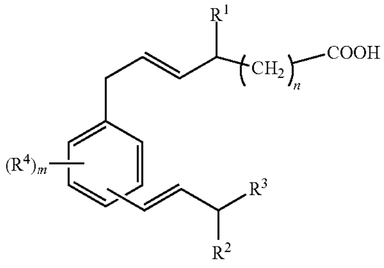

(1')

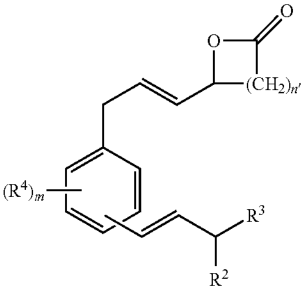

15 Claims, 3 Drawing Sheets

(56) References Cited

OTHER PUBLICATIONS

Murakami, Yuto et al., "Synthetic study of stable bioisostere in which the skipped dienes structure of anti-inflammatory lipid mediator RvE2 is replaced with a benzene ring" Mar. 5, 2019, 22T-am07S, Abstract of the 139th Annual Meeting of the Pharmaceutical Society of Japan.
Murakami, Y. et al., "Design and Synthesis of Benzene Congeners of Resolvin E2, a Proresolving Lipid Mediator, as Its Stable Equivalents", ACS Med. Chem. Lett., Mar. 25, 2020, 11, 479-484.
Murakami,Yuto et al., Slides: Synthetic study of stable bioisostere in which the skipped dienes structure of anti-inflammatory lipid mediator RvE2 is replaced with a benzene ring, The 139th Annual Meeting of the Pharmaceutical Society of Japan, Mar. 22, 2019.
International Search Report from PCT/JP2021/006102 dated Apr. 20, 2021.

* cited by examiner

STABLE EQUIVALENT OF RESOLVIN E2

CROSS-REFERENCE TO RELATED APPLICATIONS

This application is the U.S. national stage entry of PCT/JP2021/006102, filed on Feb. 18, 2021, which claims priority to and all benefit of Japanese Patent Application No. 2020-025666, filed on Feb. 18, 2020, the entire disclosures of which are fully incorporated herein by reference.

TECHNICAL FIELD

The present invention relates to a compound that has the same anti-inflammatory action as resolvin E2 and is more stable than resolvin E2, and an anti-inflammatory agent containing the compound as an active ingredient.

BACKGROUND ART

Resolvin (Rvs), which is a metabolite of ω-3 polyunsaturated fatty acid, has a strong anti-inflammatory action (Non-Patent Document 1) and in recent years has been attracting attention as a lead of novel anti-inflammatory drugs. Rvs actively promotes the dissipation of inflammation by suppressing neutrophil infiltration and promoting phagocytosis of macrophages at a significantly lower dose. Above all, resolvin E2 (RvE2: (5S,6E,8Z,11Z,14Z,16E,18R)-5,18-dihydroxyicosa-6,8,11,14,16-pentaenoic acid) is a lipid mediator that has an extremely strong inflammatory converging action. However, Rvs is chemically and metabolically unstable due to the polyunsaturated structure thereof. As a result, it is required to develop a more stable substance while maintaining strong anti-inflammatory activity.

As a stable equivalent compound of RvE2, for example, a cyclopropane congener (a homolog) of RvE2 (CP-RvE2) has been reported (Non-Patent Document 2). The positions of the two bisallyl C10 and C13 in the skipped diene moiety of RvE2 are susceptible to oxidation. CP-RvE2 is a compound in which the cis-olefin of C11-C12 is substituted with cis-cyclopropane.

CITATION LIST

Non-Patent Documents

[Non-Patent Document 1]
Serhan and Petasis, Chemical Reviews, 2011, vol. 111 (10), p. 5922-5943.
[Non-Patent Document 2]
Fukuda et al., Organic Letters, 2016, vol. 18 (24), p. 6224-6227.
[Non-Patent Document 3]
Deyama et al., Psychopharmacology, 2018, vol. 235, p. 329-336.
[Non-Patent Document 4]
Ningzhang Zhou et al., Org. Lett., 2008, 10, 14, 3001-3004
[Non-Patent Document 5]
Jean-Martial L'Helgoual'ch et al., Chem. Commun., 2008, 5375-5377
[Non-Patent Document 6]
Gotz, K., Liermann et al., Org. Biomol. Chem., 2010, 8, 2123
[Non-Patent Document 7]
Corey, E. J. et al., J. Am. Chem. Soc., 1997, 119, 11769
[Non-Patent Document 8]
Boer, R. E. et al., Org. Lett., 2018, 20, 4020

SUMMARY OF INVENTION

Technical Problem

Although CP-RvE2 is a strong anti-inflammatory agent having improved stability with respect to oxygen as compared with RvE2, it has insufficient metabolic stability. In addition, the synthesis of CP-RvE2 requires a considerably long reaction step, resulting in a problem of a low total yield.

That is, an object of the present invention is to provide a stable equivalent of RvE2 which overcomes two problems that hinder the pharmaceutical use of RvE2, that is, both the chemical and metabolic instability and the complicated chemical synthesis.

Solution to Problem

The inventors of the present invention found that a benzene congener (BZ-RvE2) of RvE2, which is obtained by substituting the skipped diene moiety of RvE2 with a benzene ring, exhibits anti-inflammatory activity similar to RvE2, has high chemical and metabolic stability, and is synthesized relatively easily, thereby completing the present invention.

That is, the present invention provides the following compounds.

[1] A compound represented by the following General Formula (1) or (1').

(1)

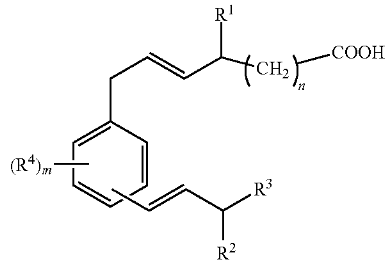

(1')

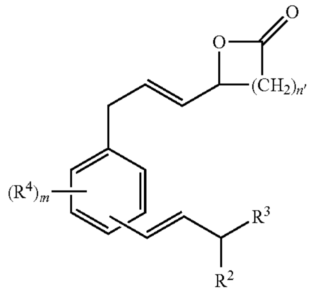

[In the formulae, $R^1$ and $R^2$ each independently represents a hydrogen atom or a hydroxy group; $R^3$ represents an alkyl group having 1 to 6 carbon atoms; $R^4$ represents a halogen atom or an alkyl group; m indicates the number of $R^4$ and represents an integer of 0 to 4; in a case where m is 2 or more, a plurality of $R^4$'s may be the same or different from each other; n represents an integer of 1 to 6; and n' represents an integer of 1 to 4.]

[2] The compound according to [1], in which the compound is represented by the following General Formula (1-o) or General Formula (1-m).

(1-o)

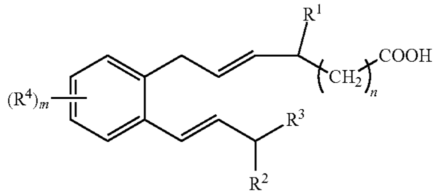

(1-m)

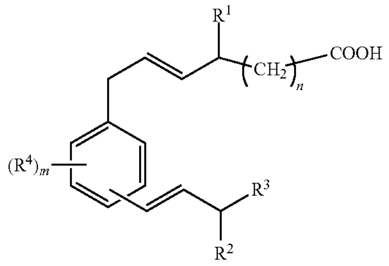

[In the formulae, $R^1$, $R^2$, $R^3$, $R^4$, m, and n are the same as $R^1$, $R^2$, $R^3$, $R^4$, m, and n in General Formula (1).]

[3] The compound according to [2], in which the compound is represented by the following General Formula (1-o-1), (1-o-2), (1-m-1), or (1-m-2).

(1-o-1)

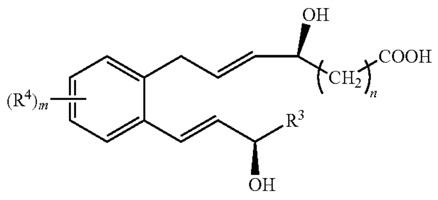

(1-o-2)

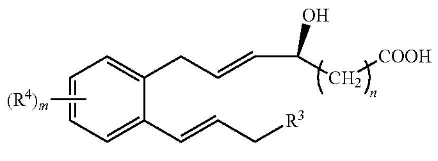

(1-m-1)

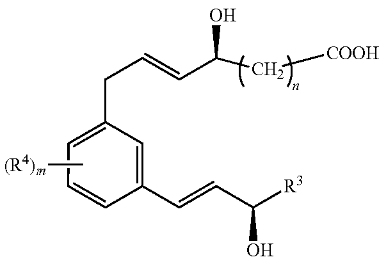

(1-m-2)

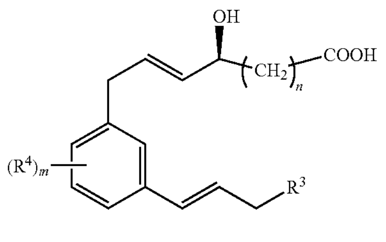

[In the formulae, $R^3$, $R^4$, m, and n are the same as $R^3$, $R^4$, m, and n in General Formula (1).]

[4] The compound according to any one of [1] to [3], in which the halogen atom is a fluorine atom, a chlorine atom, a bromine atom, or an iodine atom, and the alkyl group is a methyl group.

[5] The compound according to any one of [1] to [4], in which the halogen atom is a bromine atom.

[6] The compound according to any one of [1] to [5], in which in General Formula (1) or (1'), m represents 0 or 1.

[7] The compound according to any one of [2] to [6], in which in General Formula (1-o) or (1-m), $R^4$ is substituted at a meta-position or a para-position of a substituent having a carboxylic acid group.

[8] The compound according to [1], in which in General Formula (1'), a substituent having $R^2$ and $R^3$ is substituted at an ortho-position or a meta-position of a substituent having a lactone ring.

[9] The compound according to [8], in which in General Formula (1'), $R^4$ is substituted at the meta-position or a para-position of the substituent having the lactone ring.

[10] The compound according to [1], in which General Formula (1') is the following General Formula (1'-1) or (1'-2).

(1'-1)

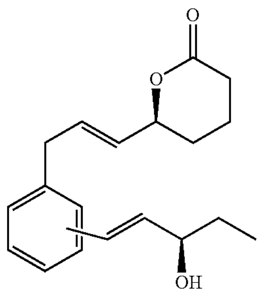

(1'-2)

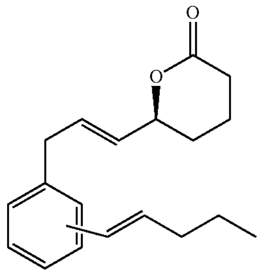

[11] A neutrophil infiltration suppressor containing, as an active ingredient, the compound according to any one of [1] to [10].

[12] An anti-inflammatory agent containing, as an active ingredient, the compound according to any one of [1] to [10].

[13] An antidepressant containing, as an active ingredient, the compound according to any one of [1] to [10].

[14] A pharmaceutical composition containing, as an active ingredient, the compound according to any one of [1] to [10].

[15] The pharmaceutical composition according to [14], in which the pharmaceutical composition is used for treating inflammation.

[16] The pharmaceutical composition according to [14], in which the pharmaceutical composition is used for treating depression.

Advantageous Effects of Invention

The compound according to the present invention exhibits anti-inflammatory activity similar to RvE2, has high chemical and metabolic stability, and is synthesized relatively easily. As a result, similar to RvE2, the compound is very useful as an active ingredient of a pharmaceutical composition that is used for the treatment of inflammatory diseases and the like.

BRIEF DESCRIPTION OF DRAWINGS

FIG. 1(*a*) is a graph showing the results of intraperitoneally administering 300 pg of RvE2, o-BZ-RvE2, m-BZ-RvE2, p-BZ-RvE2, or only a solvent to an acute inflammation model mouse, and collecting peritoneal exudate to count the number of neutrophils. FIG. 1(*b*) is a graph showing the results of intraperitoneally administering 300 fg, 300 pg, or 300 ng of RvE2 or o-BZ-RvE2, or only a solvent to an acute inflammation model mouse, and collecting peritoneal exudate to count the number of neutrophils.

DESCRIPTION OF EMBODIMENTS

Figure 1:
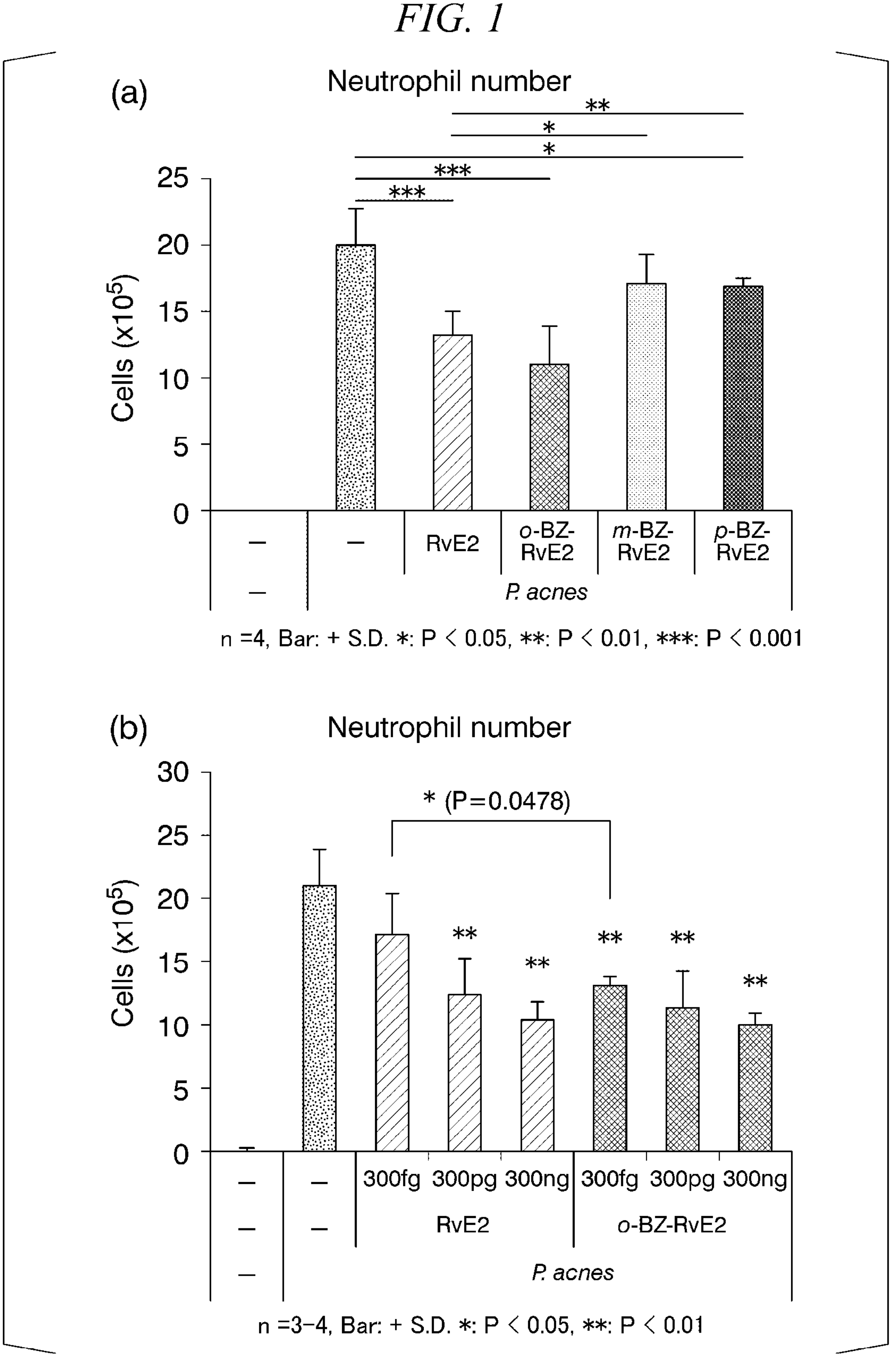
FIG. 1 is graphs showing the results of carrying out anti-inflammatory property evaluation assays of RvE2, o-BZ-RvE2, m-BZ-RvE2, and p-BZ-RvE2 in Example 1.

In the present invention and the present specification, "$C_{y\text{-}z}$ (y and z are a positive integer satisfying $y<z$)" means that the number of carbon atoms is equal to or more than y and equal to or less than z.

In the present invention and the present specification, the "compound represented by Formula (X)" may be represented by the "compound (X)".

The compound according to the present invention is a compound represented by General Formula (1) or (1') (hereinafter, may be referred to as a "compound (1)" or a "compound (1')"). The compounds (1) and (1') are BZ-RvE2, in which the skipped diene moiety of RvE2 is substituted with a benzene ring, and a congener thereof. The compounds (1) and (1') are chemically and metabolically stable since the less stable diene moiety is substituted with a highly stable benzene ring.

<Compound (1)>

(1)

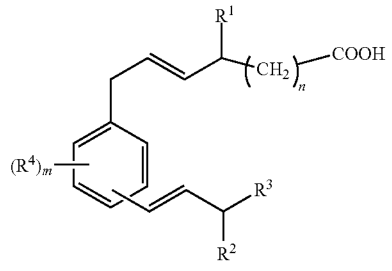

[In the formulae, $R^1$ and $R^2$ each independently represents a hydrogen atom or a hydroxy group; $R^3$ represents an alkyl group having 1 to 6 carbon atoms; $R^4$ represents a halogen atom or an alkyl group; m indicates the number of $R^4$ and represents an integer of 0 to 4; in a case where m is 2 or more, a plurality of $R^4$'s may be the same or different from each other; and n represents an integer of 1 to 6.]

In General Formula (1), m preferably represents an integer of 0 to 2, where it is more preferably 0 or 1. In General Formula (1), in a case where m represents 1 or more, $R^4$ is preferably a fluorine atom, a chlorine atom, a bromine atom, an iodine atom, or a methyl group, and in a case where m represents 1, $R^4$ is more preferably a bromine atom. In Formulae (1-o) and (1-m) described later, $R^4$ is preferably substituted at the meta-position or para-position of a substituent having a carboxylic acid group.

The compound (1) includes a compound (1-o), a compound (1-m), and a compound (1-p).

(1-o)

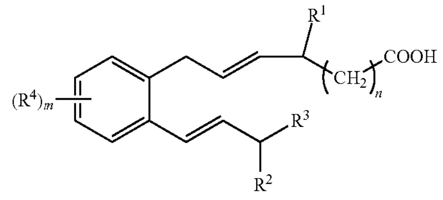

(1-m)

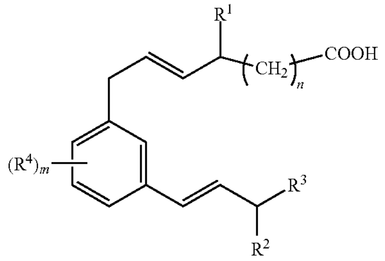

(1-p)

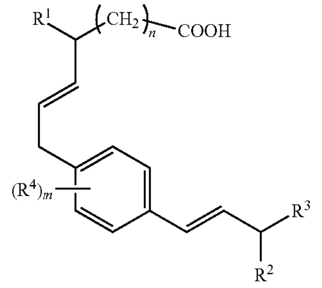

In General Formulae (1), (1-o), (1-m), and (1-p), $R^1$ and $R^2$ each independently represents a hydrogen atom or a hydroxy group. The compound (1), the compound (1-o), the compound (1-m), and the compound (1-p) are preferably a compound in which $R^1$ represents a hydroxy group and $R^2$ represents a hydrogen atom or a compound in which both $R^1$ and $R^2$ represent a hydroxy group, and they are particularly preferably a compound in which $R^1$ represents a hydroxy group and $R^2$ represents a hydrogen atom.

In General Formulae (1), (1-o), (1-m), and (1-p), $R^3$ represents an alkyl group having 1 to 6 carbon atoms (a $C_{1-6}$ alkyl group). The $C_{1-6}$ alkyl group may be linear or may be branched. Examples of the $C_{1-6}$ alkyl group include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, and a hexyl group. The compound (1), the compound (1-o), the compound (1-m), and the compound (1-p) are preferably a compound in which $R^3$ represents a $C_{1-4}$ alkyl group, more preferably a compound in which $R^3$ represents a linear $C_{1-4}$ alkyl group, still more preferably a compound in which $R^3$ represents a methyl group, an ethyl group, or a propyl group, and particularly preferably a compound in which $R^3$ represents an ethyl group.

In General Formulae (1), (1-o), (1-m), and (1-p), n represents an integer of 1 to 6. The compound (1), the compound (1-o), the compound (1-m), and the compound (1-p) are preferably a compound in which n represents an integer of 2 to 5, more preferably a compound in which n represents an integer of 2 to 4, and particularly preferably a compound in which n represents an integer of 3.

In General Formulae (1-o) or (1-m), $R^4$ and m are the same as those in General Formula (1).

The compound (1) is preferably the compound (1-o) or the compound (1-m), and more preferably the compound (1-o) since the in vivo metabolic stability is more excellent. Examples of the compound (1-o) include compounds (1-o-1) to (1-o-4), and examples of the compound (1-m) include compounds (1-m-1) to compounds (1-m-4). The compound (1) is preferably a compound represented by General Formula (1-o-1), (1-o-2), (1-m-1), or (1-m-2), more preferably a compound represented by General Formula (1-o-2) or (1-m-2), and still more preferably a compound represented by General Formula (1-o-2), since the anti-inflammatory action including a neutrophil infiltration suppressive effect is more excellent.

(1-o-1)

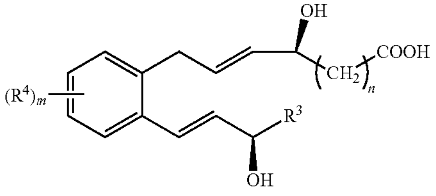

(1-o-2)

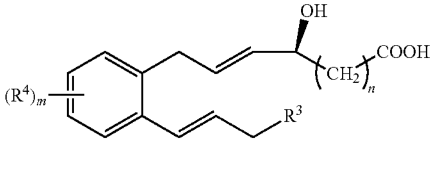

-continued (1-o-3)

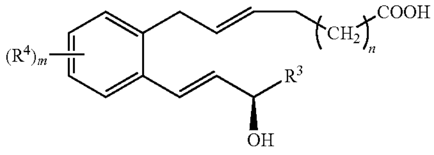

(1-o-4)

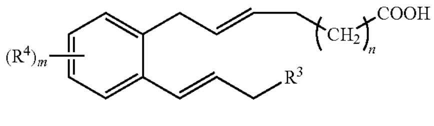

(1-m-1)

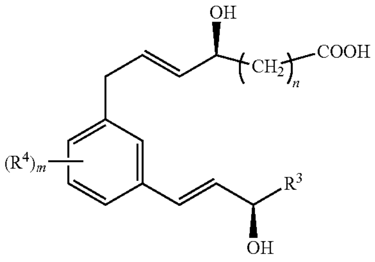

(1-m-2)

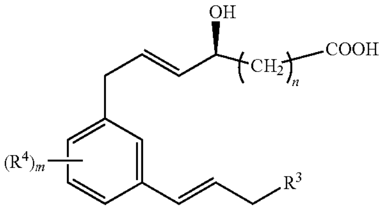

(1-m-3)

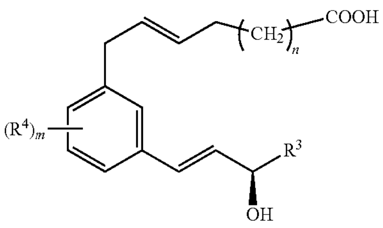

(1-m-4)

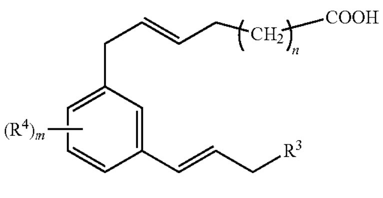

In General Formulae (1-o-1) to (1-o-4) and (1-m-1) to (1-m-4), $R^3$, $R^4$, m, and n are the same as those in General Formulae (1). The compound represented by these general formulae is preferably a compound in which $R^3$ represents a linear $C_{1-4}$ alkyl group and n represents an integer of 2 to 4, and is more preferably a compound in which $R^3$ represents a methyl group, an ethyl group, or a propyl group, and n represents an integer of 2 to 4.

<Compound (1')>

(1')

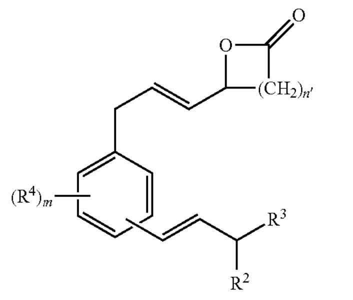

In General Formula (1'), $R^2$, $R^3$, $R^4$, and m are the same as those in General Formula (1). n' represents an integer of 1 to 4, and is preferably 3. In General Formula (1'), the substituent having $R^2$ and $R^3$ is preferably substituted at the ortho-position or the meta-position of a substituent having a lactone ring. In this case, $R^4$ is preferably substituted at the meta-position or the para-position of the substituent having a lactone ring.

The compound (1') is preferably a compound represented by Formula (1'-1) or (1'-2).

(1'-1)

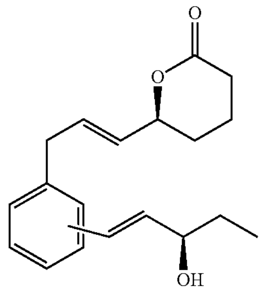

(1'-2)

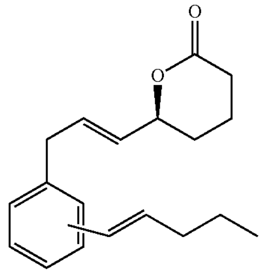

The compound (1) may form a salt. Examples of the base that forms the salt include alkali metals such as sodium and potassium; and alkaline earth metals such as calcium and magnesium. Further, the compounds (1) and (1') may be in a form of a hydrate or the like. For example, the carboxy group in the compound (1) may form a salt with an alkali metal such as sodium or potassium.

The compounds (1) and (1') can be synthesized, for example, by linking the W-terminal chain portion and the carboxylic acid chain portion of RvE2 to a benzene ring by the Stille coupling reaction or the like, as shown in Examples below. Since the synthetic reaction can be carried out under relatively mild reaction conditions by using a stable benzene compound as a raw material, the compounds (1) and (1') are chemically synthesized easily as compared with RvE2 and CP-RvE2.

The compounds (1) and (1') are stable equivalents of RvE2 and have the same pharmacological action as RvE2. For example, similar to RvE2, the compounds (1) and (1') have an inflammatory converging action. For this reason, the compounds (1) and (1') and salts thereof are very useful as an active ingredient of a pharmaceutical composition that is used for the treatment of diseases in which therapeutic or preventive effects are expected due to the inflammatory converging action, and in particular, they are suitable as an active ingredient of a pharmaceutical composition for the treatment or prevention of inflammation and inflammatory diseases. Examples of the inflammatory disease include inflammatory bowel diseases such as ulcerative colitis and Crohn's disease, allergic diseases such as allergic dermatomyositis, asthma, and allergic rhinitis, and autoimmune diseases such as rheumatoid arthritis, collagen disease, systemic erythematosus, polymyositis and dermatomyositis, and Sjogren's syndrome. In addition, similar to RvE2, the compounds (1) and (1') are useful as an active ingredient of a pharmaceutical composition that is used for the treatment or prevention of depression (Non-Patent Document 3).

Since the compound (1) or (1'), or a salt thereof is a low-molecular-weight compound, there is no problem such as immunogenicity. In addition, oral administration is also possible, and the route of administration is not greatly restricted. As a result, the compound (1) or (1'), or a salt thereof is particularly useful as an active ingredient of a pharmaceutical for mammals including humans.

In a case where the compound (1) or (1'), or a salt thereof is incorporated into a pharmaceutical composition, it can be blended with a pharmaceutically acceptable carrier as necessary, and various administration forms can be adopted depending on the prophylactic or therapeutic purpose. Examples of the form include an oral agent, an injection agent, a suppository, an ointment, and a patch, where an oral agent is preferable. Each of these administration forms can be produced according to a conventional formulation method known to those skilled in the art.

As the pharmaceutically acceptable carrier, it is possible to use an excipient, a binding agent, a disintegrating agent, a lubricant, a coloring agent in a solid formulation; and a solvent, a lysis auxiliary agent, a suspending agent, an isotonicizing agent, a buffer and a soothing agent in a liquid formulation. Further, as necessary, it is possible to use formulation additives such as a preservative, an antioxidant, a coloring agent, a sweetening agent, and a stabilizer.

In a case of preparing an oral solid formulation, it is possible to add an excipient to the compound (1) or (1'), and to add, as necessary, a binding agent, a disintegrating agent, a lubricant, a coloring agent, a taste-improving and flavoring agent, and the like to the compound (1) or (1'), thereby producing a tablet, a coated tablet, a granule agent, a powder agent, a capsule agent according to conventional methods.

In a case of preparing an oral liquid formulation, it is possible to add a taste-improving agent, a buffering agent, a stabilizer, a flavoring agent, and the like to the compound (1) or (1'), thereby producing an internal liquid agent, a syrup agent, and an elixir according to conventional methods.

In a case of preparing an injection agent, it is possible to add a pH-adjusting agent, a buffering agent, a stabilizer, an isotonicizing agent, a local anesthetic, and the like to the compound (1) or (1'), thereby producing subcutaneous, intramuscular, and intravenous injection agents according to conventional methods.

In a case of preparing a suppository, it is possible to add a pharmaceutical carrier known in the art, such as polyethylene glycol, lanolin, cocoa butter, fatty acid triglyceride, or the like to the compound (1) or (1'), thereby producing the suppository according to a conventional method.

In a case of preparing an ointment, a base agent, a stabilizer, a wetting agent, a preservative, and the like, which are generally used, are blended, as necessary, with the compound (1) or (1') and mixed and formulated according to conventional methods.

In a case of preparing a patch, it suffices that the ointment described above, cream, gel, a paste, and the like may be applied onto a general support according to conventional methods.

The content of the compound (1) or (1') in each of the above-described formulations is not constant depending on the patient's symptoms, the formulation form of the formulation, and the like. However, it is generally about 0.05 to 1,000 mg in an oral agent, about 0.01 to 500 mg in an injection agent, and about 1 to 1,000 mg in a suppository.

In addition, the daily dose of these formulations varies depending on the symptoms, body weight, age, gender, and the like of a patient, and thus it cannot be unconditionally determined. However, in general, the daily dose of the compound (1) or (1') for an adult (body weight: 60 kg) is about 0.05 to 5,000 mg and preferably 0.1 to 1,000 mg, and it is preferable to administer this once a day or dividedly 2 to 3 times a day.

The animal to which each of the neutrophil infiltration suppressor, the anti-inflammatory agent, and the pharmaceutical composition, which contain the compound (1) or (1') as an active ingredient, is administered is not particularly limited, and may be a human or may be an animal other than a human. Examples of a non-human animal include mammals such as a cow, a pig, a horse, a sheep, a goat, a monkey, a dog, a cat, a rabbit, a mouse, a rat, a hamster, and a guinea pig; and birds such as a chicken, a quail, and a duck.

EXAMPLES

Next, the present invention will be described in more detail by showing Examples; however, the present invention is not limited to the Examples below.

<Compound Analysis Method>

NMR spectra were measured with NMR apparatuses, JEOL ECX400P (400 MHz), JEOL EXP400 (400 MHz), and JEOL ECA500 (500 MHz) (all, manufactured by JEOL Ltd.). The chemical shift has been reported, in terms of the δ scale with respect to tetramethyl silane (TMS), as the internal standard as a value of 0.00 ppm with respect to $^1H$ ($CDCl_3$), and as residual $CHCl_3$ (as a value of 7.26 ppm with respect to $^1H$ and 77.16 ppm with respect to $^{13}C$) and as $CH_3OH$ (as a value of 3.31 ppm with respect to $^1H$ and 49.0 ppm with respect to $^{13}C$).

Mass spectra (MS) were measured with mass spectrometers, JEOL JMS-HX110, JEOL JMS-T100GCV, JEOL JMS-T100LCP, and JEOL JMS-700TZ (ESI) (all, manufactured by JEOL Ltd.).

The optical rotation degree was measured using a polarimeter DIP-1030 (manufactured by JASCO Corporation).

In silica gel column chromatography and flash column chromatography, Wakogel 60N (manufactured by Wako Pure Chemical Corporation, neutral, 63 to 212 μm) and silica gel 60N (manufactured by Kanto Chemical Co., Inc., spherical, neutral, 40 to 50 m) were used for the measurement, respectively.

Unless otherwise specified, all reactions were carried out in an argon atmosphere using glassware dried over an open fire or in an oven and monitored by analytical TLC (TLC silica gel 60 F254, manufactured by Merck KGaA).

<Animal Experiment>

All animal procedures were carried out in accordance with the Animal Ethics Committee rules, Hokkaido University, Japan.

<Anti-Inflammatory Property Evaluation Assay>

The strength of the anti-inflammatory action of each compound was evaluated by using a mouse acute inflammation model induced by intraperitoneally transplanting *Propionibacterium acnes*.

The mouse acute inflammation model was produced using male BALB/c mice (6 to 7 weeks, obtained from Japan SLC Inc.). First, *Propionibacterium acnes* (*P. acnes;* 500 μg per mouse) subjected to heat sterilization was intraperitoneally injected into a mouse to prepare an acute inflammation model mouse. Eight or twelve hours after the injection of *Propionibacterium acnes*, the test compound was intraperitoneally administered to an acute inflammation model mouse. Then, 24 hours after the injection of *Propionibacterium acnes*, a peritoneal exudate was collected and the number of neutrophils was counted.

<Evaluation of Metabolic Stability>

60 μL was aliquoted from an ethanol solution (1 mg/1 mL) of the synthetic compound to be evaluated, and the solvent was removed. A 0.1 M PBS buffer (435 μL, pH 7.4), $CH_3CN$ (10 μL), an NADPH regeneration system A solution (25 μL), and an NADPH regeneration system B solution (5 μL) were added to each compound, and stirring was carried out with a vortex mixer. After incubating the obtained reaction solution at 37 °C for 5 minutes, human liver microsomes (Corning (registered trade name) UltraPool (registered trade name) HLM 150) (25 μL) were added thereto, and 80 μL of the solution was aliquoted every hour (after 0, 1, 2, 3, and 6 hours from the addition). Each of the aliquoted solutions was quenched by adding $CH_3CN$ (80 μL) and then centrifuged (10,000 rpm) for 3 minutes at room temperature. The supernatant was collected and analyzed by using HPLC (COSMOSIL 5C18-MS-II, 4.6 mm×250 mm, $CH_3CN/H_2O/TFA$=35/65/0.01, 1.0 mL/min, detection at 254 nm).

Example 1

2-Iodobenzyl alcohol was sequentially linked to vinylstanane by Stille coupling, followed by deprotection and hydrolysis, thereby synthesizing o-BZ-RvE2 [a compound of General Formula (1-o-1) in which $R^3$ represents an ethyl group, m represents 0, and n represent 3]. By using the corresponding iodobenzyl alcohol from the same pathway, m-BZ-RvE2 [a compound of General Formula (1-m-1) in which $R^3$ represents an ethyl group, m represents 0, and n represents 3] and p-BZ-RvE2 [a compound of General Formula (1-p) in which $R^1$ and $R^2$ represent a hydroxy group, $R^3$ represents an ethyl group, m represents 0, and n represents 3] were also synthesized.

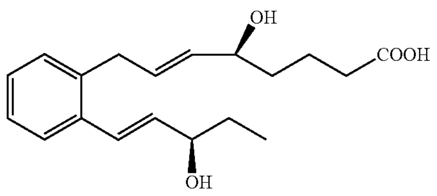

o-BZ-RvE2

-continued

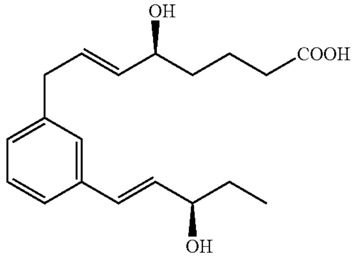

m-BZ-RvE2

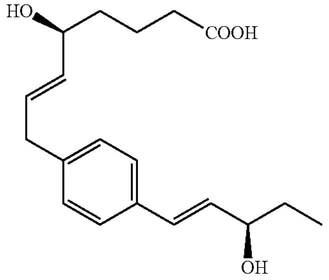

p-BZ-RvE2

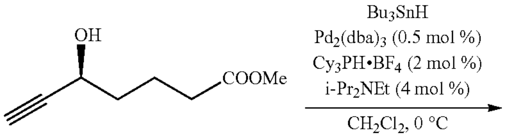

S1

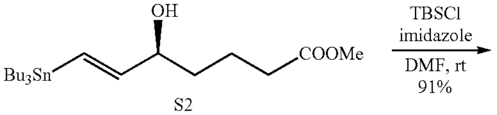

S2

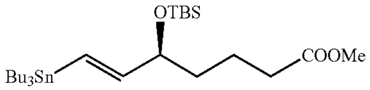

8

Methyl (S,E)-5-hydroxy-7-(tributylstannyl)hept-6-enoate (S2)

$Pd_2(dba)_3$ (55 mg, 60 μmol) was added to a $CH_2Cl_2$ (60 mL) solution of $Cy_3PH{\cdot}BF_4$ (88.0 mg, 0.24 mmol) and i-$Pr_2NEt$ (84 μL, 0.48 mmol) at room temperature. The obtained solution was stirred at the same temperature for 10 minutes. The reaction mixture was added at 0 °C to a $CH_2Cl_2$ solution containing a compound S1 (1.87 g, 12.0 mmol, >99% ee) and $Bu_3SnH$ (3.9 mL, 14.4 mmol), and then the mixture was stirred and concentrated overnight at the same temperature. The obtained residue was purified by silica gel column chromatography ($K_2CO_3$—$SiO_2$=1:9, AcOEt-hexane=1:8) to obtain a compound S2 (3.5 g, 7.83 mmol, 65%) as a colorless oil. The analysis results of the compound S2 are as follows, which are consistent with the previous report.

$^1H$ NMR (400 MHz, $CDCl_3$) δ 6.15 (dd, J=19.2, 1.0 Hz, 1H), 5.99 (dd, J=19.2, 5.2 Hz, 1H), 4.08 (m, 1H), 3.67 (s, 3H), 2.36 (t, J=7.6 Hz, 2H), 1.78-1.65 (m, 2H), 1.61-1.54 (m, 2H), 1.53-1.45 (m, 6H), 1.30 (sextuplet, J=7.2 Hz, 6H), 0.91-0.87 (m, 15H).

Methyl (S,E)-5-((tert-butyldimethylsilyl)oxy)-7-(tributylstannyl)hept-6-enoate (8)

After stirring a solution of the compound S2 (3.5 g, 7.83 mmol) in DMF (52 mL), imidazole (2.13 g, 31.3 mmol) and TBSCl (2.36 g, 15.7 mmol) were added thereto at room temperature. The obtained mixture was stirred at the same temperature for 12 hours, quenched by the addition of water, and then extracted with AcOEt/hexane (1:4). All the obtained organic extracts were mixed, washed with brine, dried with sodium sulfate ($Na_2SO_4$), and concentrated. The obtained residue was purified by flash silica gel column chromatography ($K_2CO_3$—$SiO_2$=1:9, AcOEt-hexane=1:8) to obtain a compound (8) (4.0 g, 7.12 mmol, 91%) as a colorless oil. The analysis results of the compound (8) are as follows, which are consistent with the previous report.

$^1H$ NMR (400 MHz, $CDCl_3$) δ 6.04 (d, J=19.2 Hz, 1H), 5.89 (dd, J=19.2, 6.0 Hz, 1H), 4.04 (dt, J=6.0, 6.0 Hz, 1H), 3.66 (s, 3H), 2.32 (t, J=7.4 Hz, 2H), 1.72-1.59 (m, 2H), 1.55-1.40 (m, 8H), 1.30 (sextuplet, J=7.6 Hz, 6H), 0.90-0.85 (m, 24H), 0.04 (s, 3H), 0.02 (s, 3H).

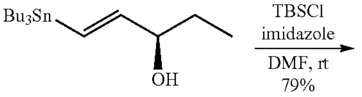

2

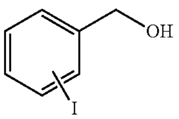

4

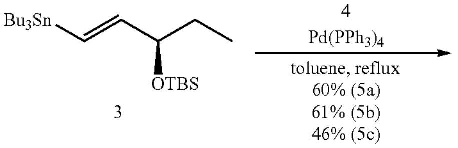

3

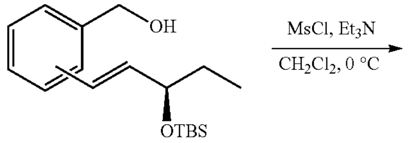

5a-c
a: o-type
b: m-type
c: p-type

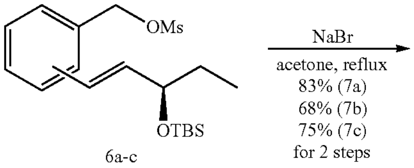

6a-c

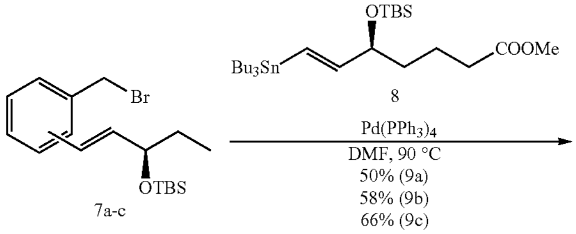

8

7a-c

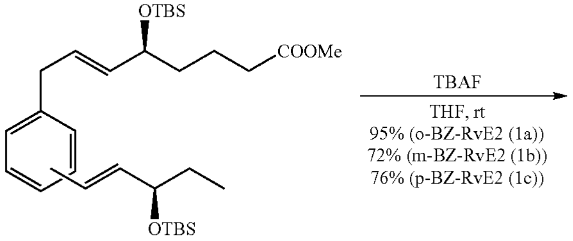

9a-c

-continued

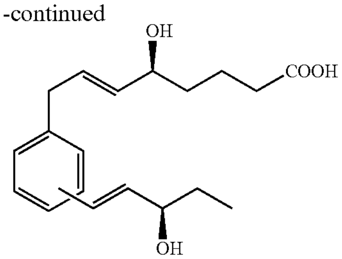

BZ-RvE2

(R,E)-1-(Tributylstannyl)pent-1-en-3-ol (3)

After stirring a solution of the compound (2) (2.0 g, 5.4 mmol, 95% ee) in DMF (52 mL), imidazole (1.47 g, 21.6 mmol) and TBSCl (1.62 g, 10.8 mmol) were added thereto at room temperature. The obtained mixture was stirred at the same temperature for 12 hours, quenched by the addition of water, and extracted with AcOEt/hexane (1:4). All the obtained organic extracts were mixed, washed with brine, dried with sodium sulfate, and concentrated. The obtained residue was purified by flash silica gel column chromatography ($K_2CO_3$—$SiO_2$=1:9, AcOEt-hexane=1:10) to obtain a compound (3) (2.1 g, 4.28 mmol, 79%) as a colorless oil. The analysis results of the compound (3) were as follows.

$[\alpha]^{15}_D$+19.2 (c 1.00, $CHCl_3$);

$^1$H NMR (500 MHz, $CDCl_3$) δ 6.01 (dd, J=19.3, 0.8 Hz, 1H), 5.91 (dd, J=19.3, 5.5 Hz, 1H), 3.96 (dt, J=5.5, 5.5 Hz, 1H), 1.54-1.40 (m, 8H), 1.30 (tq, J=7.5, 7.5 Hz, 6H), 0.94-0.81 (m, 27H), 0.05 (s, 3H), 0.04 (s, 3H);

$^{13}$C NMR (100 MHz, $CDCl_3$) δ 151.8, 126.6, 78.2, 31.0, 29.3, 27.4, 26.1, 18.5, 13.9, 10.0, 9.6; LRMS (ESI) m/z 513.25 [$(M+Na)^+$];

HRMS (EI) calcd for $C_{19}H_{41}OSSn$: 433.1949 [$(M-Bu)^+$], found: 433.1951.

(R,E)-(2-(3-((Tert-butyldimethylsilyl)oxy)pent-1-en-1-yl)phenyl)methanol (5a)

After stirring a solution of the compound (3) (510 mg, 1.04 mmol) and o-iodobenzyl alcohol (4a) (268 mg, 1.14 mmol) in toluene (10 mL), $Pd(PPh_3)_4$ (60 mg, 50 μmol) was added thereto at room temperature. The obtained mixture was refluxed overnight, quenched by the addition of a saturated aqueous solution of $NH_4Cl$, and extracted with AcOEt. All the obtained organic extracts were mixed, washed with brine, dried with sodium sulfate, and concentrated. The obtained residue was purified by flash silica gel column chromatography ($K_2CO_3$—$SiO_2$=1:9, AcOEt-hexane=1:4) to obtain a compound (5a) (191 mg, 0.623 mmol, 60%) as a yellow oil. The analysis results of the compound (5a) were as follows.

$[\alpha]^{24}_D$+31.6 (c 1.00, $CHCl_3$);

$^1$H NMR (500 MHz, $CDCl_3$) δ 7.47 (m, 1H), 7.37 (m, 1H), 7.30-7.23 (m, 2H), 6.81 (d, J=15.6 Hz, 1H), 6.11 (dd, J=16.0, 6.0 Hz, 1H), 4.75 (d, J=3.6 Hz, 2H), 4.23 (dt, J=6.4, 5.2 Hz, 1H), 1.65-1.55 (m, 3H), 0.93 (s, 9H), 0.93 (t, J=7.4 Hz, 3H), 0.10 (s, 3H), 0.07 (s, 3H);

$^{13}$C NMR (100 MHz, $CDCl_3$) δ 137.6, 136.3, 136.2, 128.3, 128.2, 127.6, 126.4, 125.7, 74.8, 63.6, 31.3, 26.0, 18.4, 9.8, −4.2, −4.6;

LRMS (ESI) m/z 329.15 [$(M+Na)^+$];

HRMS (ESI) calcd for $C_{18}H_{30}NaO_2Si$: 329.1913 [$(M+Na)^+$], found: 329.1922.

(R,E)-(3-(3-((Tert-butyldimethylsilyl)oxy)pent-1-en-1-yl)phenyl)methanol (5b)

Similar to the synthesis of the compound (5a), a compound (5b) was prepared from 3-iodobenzyl alcohol (4b) with a yield of 61%. The analysis results of the compound (5b) were as follows.

$[\alpha]^{23}_D$+37.7 (c 1.00, $CHCl_3$);

$^1$H NMR (400 MHz, $CDCl_3$) δ 7.38-7.30 (m, 3H), 7.22 (s, 1H), 6.50 (d, J=16.0 Hz, 1H), 6.20 (dd, J=16.0, 6.4 Hz, 1H), 4.69 (s, 2H), 4.20 (dt, J=6.0, 6.0 Hz, 1H), 1.70-1.56 (m, 3H), 1.08-0.76 (m, 12H), 0.08 (s, 3H), 0.05 (s, 3H);

$^{13}$C NMR (100 MHz, $CDCl_3$) δ 141.3, 137.7, 133.9, 128.9, 128.9, 126.0, 125.8, 125.0, 74.8, 65.5, 31.4, 26.1, 18.5, 9.8, −4.1, −4.6;

LRMS (ESI) m/z 329.15 [$(M+Na)^+$];

HRMS (ESI) calcd for $C_{18}H_{30}NaO_2Si$: 329.1913 [$(M+Na)^+$], found: 329.1910.

(R,E)-(4-(3-((Tert-butyldimethylsilyl)oxy)pent-1-en-1-yl)phenyl)methanol (5c)

Similar to the synthesis of the compound (5a), a compound (5c) was prepared from 4-iodobenzyl alcohol (4c) with a yield of 46%. The analysis results of the compound (5c) were as follows.

$[\alpha]^{25}_D$+44.3 (c 1.00, $CHCl_3$);

$^1$H NMR (400 MHz, $CDCl_3$) δ 7.37 (d, J=8.4 Hz, 2H), 7.31 (d, J=8.4 Hz, 2H), 6.49 (d, J=16.0 Hz, 1H), 6.17 (dd, J=16.0, 6.4 Hz, 1H), 4.68 (d, J=4.0 Hz, 2H), 4.20 (dt, J=6.0, 6.0 Hz, 1H), 1.64-1.56 (m, 2H), 0.92 (s, 9H), 0.92 (t, J=7.6 Hz, 3H), 0.08 (s, 3H), 0.05 (s, 3H);

$^{13}$C NMR (100 MHz, $CDCl_3$) δ 140.0, 136.9, 133.6, 128.7, 127.4, 126.7, 74.9, 65.3, 31.4, 26.1, 18.5, 9.8, −4.1, −4.6;

LRMS (ESI) m/z 329.10 [$(M+Na)^+$];

HRMS (ESI) calcd for $C_{18}H_{30}NaO_2Si$: 329.1913 [$(M+Na)^+$], found: 329.1915.

(R,E)-((1-(2-(Bromomethyl)phenyl)pent-1-en-3-yl)oxy)(tert-butyl)dimethylsilane (7a)

A solution of the compound (5a) (6.0 mg, 20 μmol) and $Et_3N$ (3.0 μL, 22 μmol) in $CH_2Cl_2$ (0.2 mL) was stirred, and MsCl (2.0 μL, 22 μmol) was added thereto at 0 °C. The obtained mixture was stirred at the same temperature for 1 hour, quenched by the addition of brine, and extracted with AcOEt. All the obtained organic extracts were mixed, dried with sodium sulfate, and concentrated to obtain a crude compound (6a).

A solution of the crude compound (6a) in acetone (0.2 mL) was stirred, and NaBr (6.0 mg, 58 μmol) was added thereto at room temperature. The obtained mixture was refluxed for 12 hours, quenched by the addition of brine, and extracted with AcOEt. All the obtained organic extracts were mixed, dried with sodium sulfate, and concentrated. The obtained residue was purified by silica gel column chromatography (AcOEt-hexane=1:20) to obtain a compound (7a) (6.0 mg, 16 μmol, 83% for 2 steps) as a colorless oil. The analysis results of the compound (7a) were as follows.

$[\alpha]^{21}_D$+20.6 (c 1.00, $CHCl_3$);

$^1$H NMR (400 MHz, $CDCl_3$) δ 7.46 (d, J=8.0 Hz 1H), 7.30 (m, 2H), 7.21 (m, 1H), 6.86 (d J=15.6 Hz, 1H), 6.16 (dd, J=16.0, 6.0 Hz, 1H), 4.55 (d, J=2.8 Hz, 2H), 4.27 (dt, J=6.0, 6.0 Hz, 1H), 1.62 (m, 2H), 0.95 (t, J=7.2 Hz, 3H), 0.95 (s, 9H), 0.11 (s, 3H), 0.10 (s, 3H);

$^{13}C$ NMR (100 MHz, $CDCl_3$) δ 137.2, 136.8, 134.7, 130.4, 129.2, 127.7, 126.9, 125.3, 74.6, 31.9, 31.3, 26.1, 18.4, 9.7, −4.1, −4.6;

LRMS (ESI) m/z 369.35 [$(M+H)^+$];

HRMS (EI) calcd for $C_{16}H_{24}BrOSi$: 339.0780 [$(M-Et)^+$], found: 339.0779.

(R,E)-((1-(3-(Bromomethyl)phenyl)pent-1-en-3-yl) oxy)(tert-butyl)dimethylsilane (7b)

Similar to the synthesis of the compound (7a), a compound (7b) was prepared from the compound (5b) with a yield of 68%. The analysis results of the compound (7b) were as follows.

$[\alpha]^{23}_D$+32.9 (c 1.25, $CHCl_3$);

$^1H$ NMR (400 MHz, $CDCl_3$) δ 7.37 (s, 1H), 7.31-7.20 (m, 3H), 6.48 (d, J=16.4 Hz, 1H), 6.20 (dd, J=16.0, 6.0 Hz, 1H), 4.49 (s, 2H), 4.20 (dt, J=6.0, 6.0 Hz, 1H), 1.59 (m, 2H), 0.95-0.89 (m, 12H), 0.08 (s, 3H), 0.06 (s, 3H);

$^{13}C$ NMR (100 MHz, $CDCl_3$) δ 138.5, 138.4, 134.6, 129.5, 128.8, 128.3, 127.4, 126.9, 75.0, 34.0, 31.7, 26.4, 18.8, 10.1, −3.8, −4.3;

LRMS (ESI) m/z 369.15 [$(M+H)^+$];

HRMS (EI) calcd for $C_{18}H_{29}BrOSi$: 368.1171 ($M^+$), found: 368.1173.

(R,E)-((1-(4-(Bromomethyl)phenyl)pent-1-en-3-yl) oxy)(tert-butyl)dimethylsilane (7c)

Similar to the synthesis of the compound (7a), a compound (7c) was prepared from the compound (5c) with a yield of 75%. The analysis results of the compound (7c) were as follows.

$[\alpha]^{23}_D$+43.1 (c 1.00, $CHCl_3$);

$^1H$ NMR (400 MHz, $CDCl_3$), δ 7.43 (s, 4H), 6.48 (dd, J=16.0, 1.6 Hz, 1H), 6.19 (dd, J=16.0, 6.4 Hz, 1H), 4.50 (s, 2H), 4.20 (m, 1H), 1.63-1.55 (m, 2H), 0.92 (m, 12H), 0.08 (s, 3H), 0.05 (s, 3H);

$^{13}C$ NMR (100 MHz, $CDCl_3$) δ 137.7, 136.8, 134.4, 129.4, 128.4, 126.9, 74.8, 33.7, 31.3, 26.1, 18.5, 9.8, −4.2, −4.6;

LRMS (ESI) m/z 391.20 [$(M+Na)^+$];

HRMS (EI) calcd for $C_{18}H_{29}BrOSi$: 368.1171 ($M^+$), found: 368.1167.

Methyl (S,E)-5-((tert-butyldimethylsilyl)oxy)-8-(2-((R,E)-3-((tert-butyldimethylsilyl)oxy)pent-1-en-1-yl)phenyl)oct-6-enoate (9a)

A solution containing the compound (7a) (60 mg, 0.162 mmol) and the compound (8) (148 mg, 0.243 mmol) in DMF (1.8 mL) was stirred, and $Pd(PPh_3)_4$(9.0 mg, 8.0 μmol) was added thereto at room temperature. The obtained mixture was heated to 90 °C overnight, quenched by the addition of brine, and extracted with $Et_2O$. All the obtained organic extracts were mixed, dried with sodium sulfate, and concentrated. The obtained residue was purified by silica gel column chromatography ($K_2CO_3$—$SiO_2$=1:9, AcOEt-hexane=1:8) and EPCLC (conditions: Yamazen Ultra Pack Si-40A, hexane:AcOEt=97:3, flow rate: 10 mL/minute, detection: UV 254 nm) to obtain a compound (9a) (45 mg, 80 μmol, 50%) as a colorless oil. The analysis results of the compound (9a) were as follows.

$[\alpha]^{19}_D$+7.21 (c 0.80, $CHCl_3$);

$^1H$ NMR (400 MHz, $CDCl_3$) δ 7.42 (m, 1H), 7.19-7.15 (m, 2H), 7.11 (m, 1H), 6.71 (d, J=16.0 Hz, 1H), 6.03 (dd, J=16.0, 6.4 Hz, 1H), 5.70 (dt, J=15.2, 6.4 Hz, 1H), 5.38 (dd, J=15.6, 6.8 Hz, 1H), 4.20 (dt, J=6.0, 6.0 Hz, 1H), 4.07 (dt, J=6.0, 6.0 Hz, 1H), 3.66 (s, 3H), 3.38 (d, J=6.4 Hz, 2H), 2.29 (t, J=7.6 Hz, 2H), 1.70-1.55 (m, 4H), 1.51-1.41 (m, 2H), 0.92 (t, J=7.6 Hz, 3H), 0.92 (s, 9H), 0.86 (s, 9H), 0.09 (s, 3H), 0.06 (s, 3H), 0.01 (s, 3H), −0.03 (s, 3H);

$^{13}C$ NMR (100 MHz, $CDCl_3$) δ 174.2, 137.5, 136.3, 135.4, 134.9, 129.6, 128.6, 127.5, 126.7, 126.6, 126.3, 75.0, 73.2, 51.6, 37.8, 35.8, 34.1, 31.4, 26.1, 26.0, 21.0, 18.4, 18.3, 9.9, −4.1, −4.1, −4.6, −4.7;

LRMS (ESI) m/z 583.35 [$(M+Na)^+$];

HRMS (ESI) calcd for $C_{32}H_{56}NaO_4Si_2$: 583.3615 [$(M+Na)^+$], found: 583.3636.

Methyl (S,E)-5-((tert-butyldimethylsilyl)oxy)-8-(3-((R,E)-3-((tert-butyldimethylsilyl)oxy)pent-1-en-1-yl)phenyl)oct-6-enoate (9b)

Similar to the synthesis of the compound (9a), a compound (9b) was prepared from the compound (7b) with a yield of 58%. The analysis results of the compound (9b) were as follows.

$[\alpha]^{19}_D$+16.9 (c 1.00, $CHCl_3$);

$^1H$ NMR (400 MHz, $CDCl_3$) δ 7.26-7.16 (m, 3H), 7.03 (d, J=6.8 Hz, 1H), 6.45 (d, J=16.0 Hz, 1H), 6.15 (dd, J=16.0, 6.4 Hz, 1H), 5.69 (dt, J=15.2, 6.8 Hz, 1H), 5.48 (dd, J=15.2, 6.4 Hz, 1H), 4.19 (dt, J=6.0, 6.0 Hz, 1H), 4.10 (dt, J=6.4, 6.4 Hz, 1H), 3.66 (s, 3H), 3.34 (d, J=6.4 Hz, 2H), 2.31 (t, J=7.6 Hz, 2H), 1.68-1.47 (m, 6H), 0.92-0.87 (m, 21H), 0.08 (s, 3H), 0.05 (s, 3H), 0.03 (s, 3H), 0.01 (s, 3H);

$^{13}C$ NMR (100 MHz, $CDCl_3$) δ 174.2, 140.7, 137.5, 135.1, 133.4, 129.2, 129.1, 128.7, 127.7, 126.7, 124.3, 75.0, 73.2, 51.6, 38.7, 37.9, 34.2, 31.4, 26.1, 26.0, 21.0, 18.5, 18.4, 9.8, 0.14, −4.0, −4.1, −4.6, −4.6;

LRMS (ESI) m/z 583.35 [$(M+Na)^+$];

HRMS (ESI) calcd for $C_{32}H_{56}NaO_4Si_2$: 583.3615 [$(M+Na)^+$], found: 583.3631.

Methyl (S,E)-5-((tert-butyldimethylsilyl)oxy)-8-(4-((R,E)-3-((tert-butyldimethylsilyl)oxy)pent-1-en-1-yl)phenyl)oct-6-enoate (9c)

Similar to the synthesis of the compound (9a), a compound (9c) was prepared from the compound (7c) with a yield of 66%. The analysis results of the compound (9c) were as follows.

$[\alpha]^{18}_D$+29.0 (c 1.10, $CHCl_3$);

$^1H$ NMR (500 MHz, $CDCl_3$) δ 7.29 (d, J=8.0 Hz, 2H), 7.11 (d, J=8.0 Hz, 2H), 6.45 (d, J=16.0 Hz, 1H), 6.13 (dd, J=16.0, 6.3 Hz, 1H), 5.67 (dt, J=15.0, 6.5 Hz, 1H), 5.46 (dd, J=15.0, 6.5 Hz, 1H), 4.18 (dt, J=6.0, 6.0 Hz, 1H), 4.09 (dt, J=6.0, 6.0 Hz, 1H), 3.66 (s, 3H), 3.33 (d, J=6.5 Hz, 2H), 2.31 (t, J=7.3 Hz, 2H), 1.70-1.44 (m, 6H), 0.95-0.79 (m, 21H), 0.08 (s, 3H), 0.05 (s, 3H), 0.03 (s, 3H), 0.01 (s, 3H);

$^{13}C$ NMR (100 MHz, $CDCl_3$) δ 174.3, 139.6, 135.2, 135.0, 132.8, 129.0, 128.9, 128.9, 126.5, 75.0, 73.2, 51.6, 38.4, 37.8, 34.2, 31.4, 26.1, 26.0, 21.0, 18.5, 18.4, 9.9, −4.0, −4.1, −4.6, −4.6;

LRMS (ESI) m/z 583.35 [$(M+Na)^+$];

HRMS (ESI) calcd for $C_{32}H_{56}NaO_4Si_2$: 583.3615 [$(M+Na)^+$], found: 583.3629.

<o-BZ-RvE2 (1a)>

A solution of the compound (9a) (5.0 mg, 8.9 μmol) in THF (18 μL) was stirred, and TBAF (1.0 M, 54 μL, 54 μmol in THF) was added thereto at room temperature. The obtained mixture was stirred at the same temperature for 24 hours. After the reaction was completed, a phosphate buffer solution (pH 6) was added to the reaction mixture, and extraction was carried out with AcOEt. All the obtained organic extracts were mixed, washed with brine, dried with sodium sulfate, and concentrated. The obtained residue was purified by flash silica gel column chromatography ($MeOH—CHCl_3$=1:30) to obtain o-BZ-RvE2 (1a) (2.7 mg, 8.5 μmol, 95%) as a colorless oil. The analysis results of o-BZ-RvE2 were as follows.

$[\alpha]^{19}_D$+1.45 (c 0.25, MeOH);

$^1H$ NMR (400 MHz, $CD_3OD$) δ 7.46 (m, 1H), 7.16 (m, 3H), 6.83 (d, J=16.0 Hz, 1H), 6.08 (dd, J=16.0, 6.4 Hz, 1H), 5.79 (dt, J=15.6, 6.0 Hz, 1H), 5.37 (dd, J=15.6, 6.8 Hz, 1H), 4.14 (dt, J=6.8, 6.8 Hz, 1H), 4.00 (dt, J=6.4, 6.4 Hz, 1H), 3.44 (d, J=6.0 Hz, 2H), 2.24 (t, J=7.2 Hz, 2H), 1.68-1.44 (m, 6H), 0.98 (t, J=7.6 Hz, 3H);

$^{13}C$ NMR (100 MHz, $CD_3OD$) δ 180.2, 138.7, 137.4, 135.5, 135.3, 130.9, 130.7, 128.8, 128.6, 127.6, 127.0, 75.1, 73.2, 38.0, 36.9, 31.3, 23.0, 10.3;

LRMS (ESI) m/z 316.95 $[(M-H)^-]$;

HRMS (ESI) calcd for $C_{19}H_{25}O_4$: 317.1753 $[(M-H)^-]$, found: 317.1749.

HPLC purity: >99% (COSMOSIL 5C18-MS-II 4.6 mm×250 mm, $CH_3CN/H_2O$/TFA=35/65/0.01, 1.0 mL/min, $t_R$=11.7 min, detection at 254 nm)

<m-BZ-RvE2 (1b)>

Similar to the synthesis of o-BZ-RvE2, m-BZ-RvE2 (1b) was prepared from the compound (9b) with a yield of 72%. The analysis results of m-BZ-RvE2 (1b) were as follows.

$[\alpha]^{19}_D$−1.31 (c 0.18, MeOH);

$^1H$ NMR (400 MHz, $CD_3OD$) δ 7.23 (m, 3H), 7.07 (m, 1H), 6.54 (d, J=16.0 Hz, 1H), 6.20 (dd, J=16.0, 6.8 Hz, 1H), 5.79 (dt, J=15.2, 6.8 Hz, 1H), 5.52 (dd, J=15.6, 6.8 Hz, 1H), 4.11 (dt, J=6.8, 6.8 Hz, 1H), 4.11 (dt, J=6.8, 6.8 Hz, 1H), 3.36 (d, J=6.8 Hz, 2H), 2.30 (t, J=7.2 Hz, 2H), 1.66-1.50 (m, 6H), 0.96 (t, J=7.2 Hz, 3H);

$^{13}C$ NMR (100 MHz, $CD_3OD$) δ 177.9, 142.1, 138.8, 135.7, 133.7, 131.5, 131.5, 129.9, 129.1, 127.9, 125.4, 75.3, 73.3, 39.7, 38.0, 35.1, 31.5, 22.5, 10.5;

LRMS (ESI) m/z 316.90 $[(M-Na)^-]$;

HRMS (ESI) calcd for $C_{19}H_{25}O_4$: 317.1753 $[(M-H)^-]$, found: 317.1746.

HPLC purity: >99% (COSMOSIL 5C18-MS-II 4.6 mm×250 mm, $CH_3CN/H_2O$/TFA=35/65/0.01, 1.0 mL/min, $t_R$=11.5 min, detection at 254 nm)

<p-BZ-RvE2 (1c)>

Similar to the synthesis of o-BZ-RvE2, p-BZ-RvE2 (1c) was prepared from the compound (9c) with a yield of 76%. The analysis results of p-BZ-RvE2 (1c) were as follows.

$[\alpha]^{18}_D$+1.77 (c 0.43, MeOH);

$^1H$ NMR (500 MHz, $CD_3OD$) δ 7.31 (d, J=8.0 Hz, 2H), 7.13 (d, J=8.0 Hz, 2H), 6.52 (d, J=16.0 Hz, 1H), 6.16 (dd, J=16.0, 6.5 Hz, 1H), 5.77 (dt, J=15.5, 6.5 Hz, 1H), 5.49 (dd, J=15.5, 7.0 Hz, 1H), 4.09 (dt, J=6.5, 6.5 Hz, 1H), 4.02 (dt, J=7.0, 7.0 Hz, 1H), 3.34 (d, J=6.5 Hz, 2H), 2.29 (t, J=7.5 Hz, 2H), 1.70-1.46 (m, 6H), 0.96 (t, J=7.5 Hz, 3H);

$^{13}C$ NMR (100 MHz, $CD_3OD$) δ 177.7, 141.0, 136.4, 135.5, 132.8, 131.2, 131.1, 129.8, 127.5, 75.1, 73.1, 39.3, 37.8, 34.9, 31.3, 22.3, 10.3;

LRMS (ESI) m/z 316.90 $[(M-Na)^-]$;

HRMS (ESI) calcd for $C_{19}H_{25}O_4$: 317.1753 $[(M-H)^-]$, found: 317.1749.

HPLC purity: 98% (COSMOSIL 5C18-MS-II 4.6 mm×250 mm, $CH_3CN/H_2O$/TFA=35/65/0.01, 1.0 mL/min, $t_R$=11.0 min, detection at 254 nm)

<Anti-Inflammatory Property Evaluation Assay>

12 hours after the injection of *Propionibacterium acnes*, 300 pg of RvE2, o-BZ-RvE2, m-BZ-RvE2, p-BZ-RvE2, or only a solvent was intraperitoneally administered to acute inflammation model mice (n=4). Then, 24 hours after the injection of *Propionibacterium acnes*, a peritoneal exudate was collected and the number of neutrophils was counted. The results are shown in FIG. 1(*a*).

12 hours after the injection of *Propionibacterium acnes*, 300 fg, 300 pg, or 300 ng of RvE2 or o-BZ-RvE2, or only a solvent was independently intraperitoneally administered to acute inflammation model mice (n=3 or 4). Then, 24 hours after the injection of *Propionibacterium acnes*, a peritoneal exudate was collected and the number of neutrophils was counted. The results are shown in FIG. 1(*b*).

As shown in FIG. 1(*a*), in any cases of o-BZ-RvE2, m-BZ-RvE2, and p-BZ-RvE2, the number of neutrophils was small as compared with a model mouse to which the solvent alone had been administered, and the infiltration of neutrophils into the abdominal cavity, which is the site of inflammation, was significantly suppressed. From this result, it was found that similar to RvE2, all of o-BZ-RvE2, m-BZ-RvE2, and p-BZ-RvE2 have an inflammatory converging action and thus are useful as an anti-inflammatory agent. In particular, o-BZ-RvE2 has an excellent anti-inflammatory action as compared with RvE2 (FIGS. 1(*a*) and 1(*b*)).

<Evaluation of Metabolic Stability>

Figure 2:
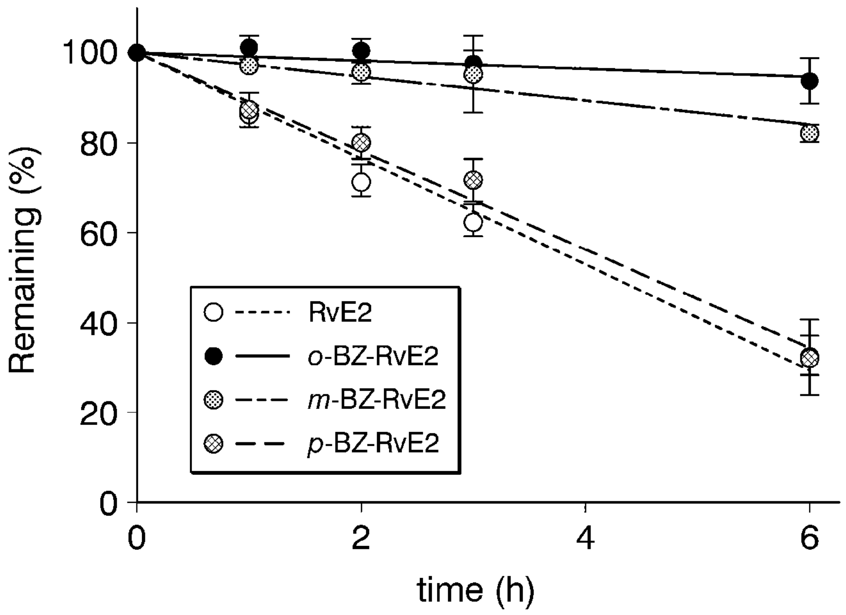
FIG. 2 is a graph showing the results of carrying out metabolic stability evaluation assays of RvE2, o-BZ-RvE2, m-BZ-RvE2, and p-BZ-RvE2 with respect to human liver microsomes in Example 1.

The metabolic stability of RvE2, o-BZ-RvE2, m-BZ-RvE2, and p-BZ-RvE2 with respect to human liver microsomes was investigated. Specifically, each of RvE2, o-BZ-RvE2, m-BZ-RvE2, and p-BZ-RvE2 was mixed with human liver microsomes, and the proportion of the temporally remaining RvE2 was investigated. The results are shown in FIG. 2. As shown in FIG. 2, similar to RvE2, p-BZ-RvE2 was easily degraded by the human liver microsomes. On the other hand, o-BZ-RvE2 and m-BZ-RvE2 had a remaining rate of 90% or more even after 6 hours had passed after being mixed with the human liver microsomes. In particular, o-BZ-RvE2 was excellent in metabolic stability.

Example 21

RvE's commonly have a carboxylic acid and a hydroxy group at the o-3 position, and RvE1 and RvE2 commonly have a hydroxy group at the 5-position. A deoxy derivative of o-BZ-RvE2 was synthesized, which has the strongest anti-inflammatory activity in Example 1, and the effect thereof on the biological activity was examined. 5-Deoxy-o-BZ-RvE2 is a compound of General Formula (1-o-3) in which $R^3$ represents an ethyl group, m represents 0, and n represents 3, 17-deoxy-o-BZ-RvE2 is a compound of General Formula (1-o-2) in which $R^3$ represents an ethyl group, m represents 0, and n represents 3, and 5,17-deoxy-o-BZ-RvE2 is a compound of General Formula (1-o-4) in which $R^3$ represents an ethyl group, m represents 0, and n represents 3.

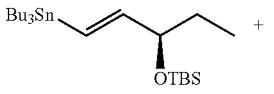

3

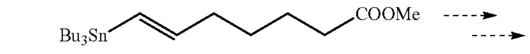

11

-continued

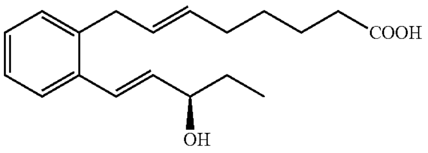

5-deoxy-o-BZ-RvE2

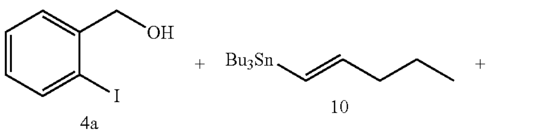

4a 10

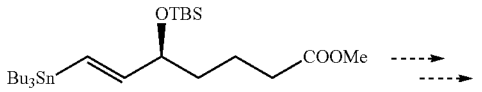

8

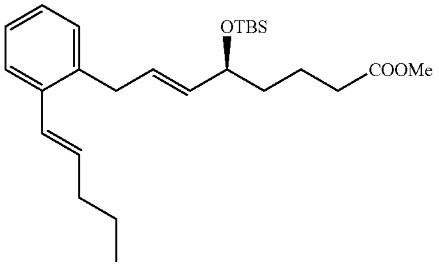

17-deoxy-o-BZ-RvE2

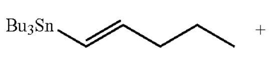

10

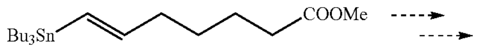

11

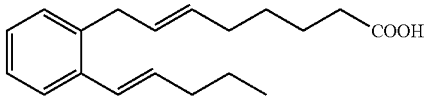

5,17-dideoxy-o-BZ-RvE2

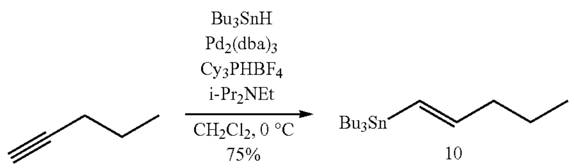

10

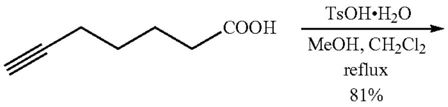

-continued

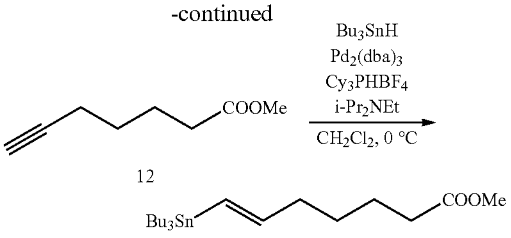

12

11

(E)-tributyl(pent-1-en-1-yl)stannane (10)

A compound (10) (2.7 g, 7.52 mmol, 75%) was synthesized from 1-pentyne (994 μL, 10.0 mmol) in the same manner as the compound (S2). The analysis results of the compound (10) were as follows.

$^1H$ NMR (500 MHz, $CDCl_3$) δ 5.95 (dt, J=19.0, 6.0 Hz, 1H), 5.86 (d, J=19.0 Hz, 1H), 2.11 (dt, J=6.5, 6.5 Hz, 2H), 1.54-1.26 (m, 15H), 1.00-0.75 (m, 19H);

$^{13}C$ NMR (100 MHz, $CDCl_3$) δ 149.8, 127.3, 40.2, 29.3, 27.4, 22.2, 13.9, 13.8, 9.5;

LRMS (EI) m/z 303.10 ($M^+$);

HRMS (EI) calcd for $C_{13}H_{27}Sn$: 303.1135 ($M^+$), found: 303.1134.

Methyl hept-6-ynoate (12)

In an argon atmosphere, p-toluenesulfonic acid (10 mg, 36.5 mmol) and methanol (900 μL) were added to a dichloromethane solution (5 mL) of 6-heptic acid (630 μL, 5.0 mmol), and heating and reflux were carried out overnight. Next, the reaction was quenched with a saturated aqueous solution of sodium hydrogen carbonate and extracted with dichloromethane. The organic layer was washed with a saturated saline solution and dried with sodium sulfate. The dried reactant was filtered through a cotton plug, the solvent was subsequently distilled off under reduced pressure, and the obtained residue was purified by silica gel chromatography (hexane:ethyl acetate=4:1) to obtain a compound (12) (530 mg, 3.78 mmol, 76%) as a yellow oil. The analysis results of the compound (12) are as follows, which are consistent with the previous report.

$^1H$ NMR (400 MHz, $CDCl_3$) δ 3.68 (s, 3H), 2.35 (t, J=7.6 Hz, 2H), 2.22 (dt, J=7.2, 2.8 Hz, 2H), 1.96 (t, J=2.8 Hz, 1H), 1.74 (m, 2H), 1.57 (m, 2H).

Methyl (E)-7-(tributylstannyl)hept-6-enoate (11)

In an argon atmosphere, tris(dibenzylideneacetone) dipalladium (0) (4.6 mg, 5 μmol, 0.5% by mole), tricyclohexylphosphonium tetrafluoroborate (7.4 mg, 20 μmol, 2% by mole), and diisopropylethylamine (7 μL, 40 μmol, 4% by mole) were stirred in a dichloromethane solution (10 mL) at room temperature. After 10 minutes, the temperature of the reaction solution was made to be 0 °C, and then the compound (12) (140 mg, 1.0 mmol) and hydrogenated tributylstannane (320 μL, 1.2 mmol, 1.2 eq.) were added thereto, and stirring was further carried out overnight. Then, the solvent was distilled off from the reaction solution under reduced pressure and purified by silica gel chromatography (10% w/w $K_2CO_3$—SiOH, hexane:ethyl acetate=10:1) to obtain a compound (11) (295 mg) as a crude product. The compound (11) was used as it was for the synthesis of a compound (16e) and a compound (16f).

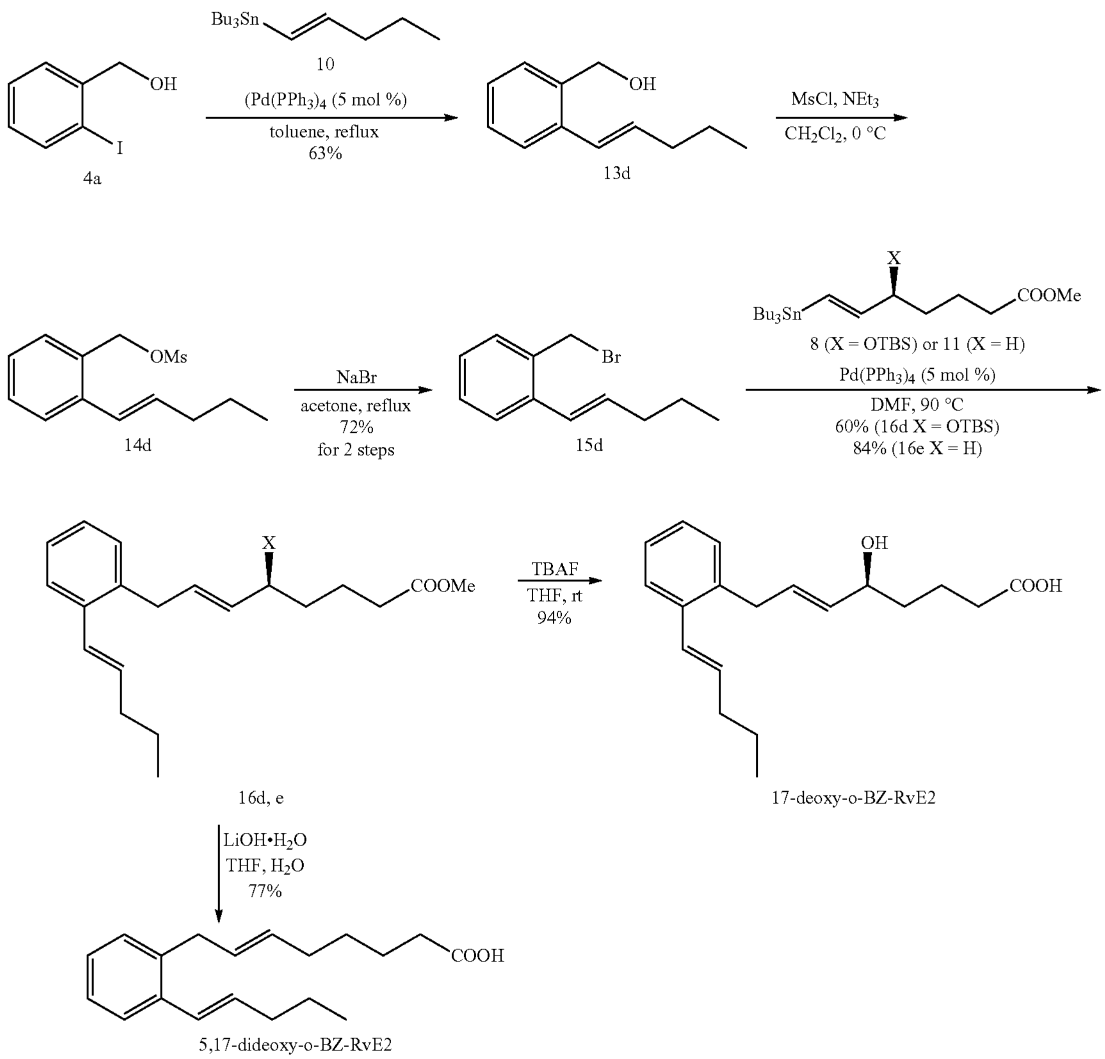

(E)-(2-(pent-1-en-1-yl)phenyl)methanol (13d)

In an argon atmosphere, the compound (10) (1.08 g, 3.0 mmol), 2-iodobenzyl alcohol (4a, 702 mg, 3.0 mmol, 1.0 eq.), and tetrakistriphenylphosphine palladium (173 mg, 0.15 mmol, 5% by mole) were frozen and degassed in a toluene solution (20 mL), and stirring was carried out overnight under heating and reflux. A saturated aqueous solution of ammonium chloride was added to the obtained reaction solution to stop the reaction, and extraction was carried out with ethyl acetate. The obtained organic layer was washed with a saturated saline solution, anhydrous sodium sulfate was added thereto, and dried. Then, the solvent was distilled off under reduced pressure, and the residue was purified by flash silica gel chromatography (10% w/w $K_2CO_3$—SiOH, hexane:ethyl acetate=10:1) to obtain a compound (13d) (323 mg, 0.65 mmol, 63%). The analysis results of the compound (13d) are as follows, which are consistent with the previous report.

$^1$H NMR (400 MHz, $CDCl_3$) δ 7.64 (d, J=7.2 Hz, 1H), 7.33 (d, J=7.2 Hz, 1H), 7.28-7.19 (m, 2H), 6.68 (d, J=15.6 Hz, 1H), 6.15 (dt, J=16.0, 6.8 Hz, 1H), 4.73 (d, J=6.0 Hz, 2H), 2.22 (dt, J=6.8, 6.8 Hz, 2H), 1.64 (m, 1H), 1.51 (tq, J=7.4, 7.4 Hz, 2H), 0.96 (t, J=7.4 Hz, 3H).

(E)-1-(bromomethyl)-2-(pent-1-en-1-yl)benzene (15d)

A compound (15d) (313 mg, 1.3 mmol, 72% for 2 steps) was synthesized from the compound (13d) (322 mg, 1.8 mmol) in the same manner as the compound (7a). The analysis results of the compound (15d) were as follows.

$^1$H NMR (400 MHz, $CDCl_3$) δ 7.46 (d, J=7.6 Hz 1H), 7.31-7.24 (m, 2H), 7.19 (d, J=7.6 Hz, 1H), 6.72 (d, J=16.0 Hz, 1H), 6.21 (dt, J=16.0, 7.2 Hz, 1H), 4.57 (s, 2H), 2.25 (ddd, J=7.6, 7.2, 1.2 Hz, 2H), 1.53 (tq, J=7.6, 7.6 Hz, 2H), 0.98 (t, J=7.6 Hz, 3H);

$^{13}$C NMR (100 MHz, $CDCl_3$) δ 138.1, 134.9, 134.5, 130.7, 129.5, 127.7, 127.0, 126.7, 35.9, 32.7, 22.9, 14.2;

HRMS (EI) calcd for $C_{12}H_{15}Br$: 238.0357 ($M^+$), found: 238.0354.

Methyl (S,E)-5-((tert-butyldimethylsilyl)oxy)-8-(2-((E)-pent-1-en-1-yl)phenyl)oct-6-enoate (16d)

A compound (16d) (51 mg, 0.118 mmol, 60%) was synthesized from the compound (15d) (48 mg, 0.2 mmol) in the same manner as the compound (9a). The analysis results of the compound (16d) were as follows.

[α]$^{19}_{D}$−0.95 (c 1.00, $CHCl_3$);

$^1H$ NMR (400 MHz, $CDCl_3$) δ 7.43 (m, 1H), 7.20-7.08 (m, 3H), 6.57 (d, J=16.0 Hz, 1H), 6.08 (dt, J=16.0, 7.2 Hz, 1H), 5.69 (dt, J=16.0, 6.4 Hz, 1H), 5.35 (dd, J=15.6, 6.8 Hz, 1H), 4.06 (ddd, J=6.4, 6.4, 6.4 Hz, 1H), 3.66 (s, 3H), 3.39 (d, J=6.4 Hz, 2H), 2.29 (t, J=7.6 Hz, 2H), 2.19 (m, 2H), 1.70-1.59 (m, 2H), 1.54-1.40 (m, 4H), 0.96 (t, J=7.2 Hz, 3H), 0.86 (s, 9H), 0.01 (s, 3H), −0.02 (s, 3H);

$^{13}C$ NMR (100 MHz, $CDCl_3$) δ 174.2, 137.1, 137.0, 134.7, 132.8, 129.6, 128.8, 127.6, 127.0, 126.5, 126.0, 77.4, 73.2, 51.6, 37.8, 36.0, 35.5, 34.1, 26.0, 22.7, 21.0, 18.4, 13.9, −4.1, −4.7;

LRMS (ESI) m/z 453.20 [(M+Na)$^+$];

HRMS (ESI) calcd for $C_{26}H_{42}NaO_3Si$: 453.2801 [(M+Na)$^+$], found: 458.2802.

Methyl (S,E)-5-hydroxy-8-(2-((R,E)-3-hydroxypent-1-en-1-yl)phenyl)oct-6-enoate (16e)

A compound (16e) (51 mg, 0.17 mmol, 84%) was synthesized from the compound (15d) (48 mg, 0.2 mmol) and the compound 11 (170 mg, 0.3 mmol) in the same manner as the compound (9a). The analysis results of the compound (16e) were as follows.

$^1H$ NMR (400 MHz, $CDCl_3$) δ 7.42 (m, 1H), 7.20-7.10 (m, 3H), 6.60 (d, J=16.0 Hz, 1H), 6.07 (dt, J=16.0, 7.2 Hz, 1H), 5.55 (dt, J=15.6, 6.8 Hz, 1H), 5.38 (dt, J=15.6, 6.8 Hz, 1H), 3.66 (s, 3H), 3.36 (d, J=5.6 Hz, 2H), 2.29 (m, 2H), 2.19 (m, 2H), 2.02 (dt, J=7.2, 7.2 Hz, 2H), 1.61 (m, 2H), 1.50 (m, 2H), 1.37 (m, 2H), 0.96 (m, 3H);

$^{13}C$ NMR (100 MHz, $CDCl_3$) δ 174.3, 137.6, 137.0, 132.7, 131.3, 129.5, 129.0, 127.7, 127.1, 126.5, 125.9, 51.6, 36.6, 35.5, 34.1, 32.3, 29.0, 24.6, 22.7, 13.9; LRMS (ESI) m/z 323.15 [(M+Na)$^+$];

HRMS (ESI) calcd for $C_{20}H_{28}NaO_2$: 323.1987 [(M+Na)$^+$], found: 323.1992.

17-Deoxy-o-BZ-RvE2

17-Deoxy-o-BZ-RvE2 (10.0 mg, 0.033 mmol, 94%) was synthesized from the compound (16d) (15 mg, 0.035 mmol) in the same manner as o-BZ-RvE2. The analysis results of 17-deoxy-o-BZ-RvE2 were as follows.

[α]$^{19}_{D}$+1.66 (c 0.33, MeOH);

$^1H$ NMR (400 MHz, $CD_3OD$) δ 7.41 (m, 1H), 7.19-7.10 (m, 3H), 6.64 (d, J=16.0 Hz, 1H), 6.09 (dt, J=16.0, 7.2 Hz, 1H), 5.77 (m, 1H), 5.36 (m, 1H), 4.00 (dt, J=6.4, 6.4 Hz, 1H), 3.41 (d, J=6.0 Hz, 2H), 2.27 (t, J=7.2 Hz, 2H), 2.21 (ddd, J=14.4, 7.2, 1.6 Hz, 2H), 1.68-1.40 (m, 6H), 0.98 (t, J=7.2 Hz, 3H);

$^{13}C$ NMR (100 MHz, $CD_3OD$) δ 177.6, 138.2, 138.0, 135.2, 133.4, 130.9, 130.7, 129.0, 128.0, 127.5, 126.9, 73.1, 37.8, 37.0, 36.4, 34.9, 23.7, 22.2, 14.1;

LRMS (ESI) m/z 301.00 [(M−Na)$^-$];

HRMS (ESI) calcd for $C_{19}H_{25}O_3$: 301.1804 [(M−H)$^-$], found: 301.1799;

HPLC purity: >99% (COSMOSIL 38020-41, $CH_3CN/H_2O$/TFA=50/50/0.01, 1.0 mL/min, $t_R$=17.6 min, detection at 254 nm).

5,17-Dideoxy-o-BZ-RvE2

In an argon atmosphere, an aqueous solution (100 μL) of lithium hydroxide monohydrate (8 mg, 0.20 mmol, 4 eq.) was added to a THF solution (100 μL) of the compound (16e) (15 mg, 0.050 mmol), and stirring was carried out at room temperature overnight. A phosphate buffer (pH 6) was added to the reaction solution, and extraction was carried out with ethyl acetate. The organic layer was washed with a saturated saline solution and dried with sodium sulfate. Then, the solvent was distilled off under reduced pressure, and the residue was purified by flash silica gel chromatography (chloroform:methanol=30:1) to obtain 5,17-dideoxy-o-BZ-RvE2 (11 mg, 0.038 mmol, 77%) as a colorless oily substance. The analysis results of 5,17-dideoxy-o-BZ-RvE2 were as follows.

$^1H$ NMR (400 MHz, $CDCl_3$) δ 11.23 (s, 1H), 7.43 (m, 1H), 7.20-7.10 (m, 3H), 6.60 (d, J=16.0 Hz, 1H), 6.08 (dt, J=16.0, 7.2 Hz, 1H), 5.57 (dt, J=15.6, 6.4 Hz, 1H), 5.39 (dt, J=15.6, 6.4 Hz, 1H), 3.37 (d, J=6.4 Hz, 2H), 2.34 (t, J=7.6 Hz, 2H), 2.20 (dt, J=6.8, 6.8 Hz, 2H), 1.63 (tt, J=7.6, 7.6 Hz, 2H), 1.55-1.36 (m, 5H), 0.96 (t, J=7.6 Hz, 3H);

$^{13}C$ NMR (100 MHz, $CD_3OD$) δ 177.7, 138.6, 138.2, 133.1, 132.1, 130.6, 130.3, 129.1, 128.0, 127.4, 126.8, 37.4, 36.4, 34.9, 33.2, 30.1, 25.6, 23.7, 14.1;

LRMS (ESI) m/z 284.95 [(M−H)$^-$];

HRMS (ESI) calcd for $C_{19}H_{25}O_2$: 285.1855 [(M−H)$^-$], found: 285.1856;

HPLC purity: 96% (COSMOSIL 38020-41, $CH_3CN/H_2O$/TFA=80/20/0.01, 1.0 mL/min, $t_R$=9.6 min, detection at 254 nm).

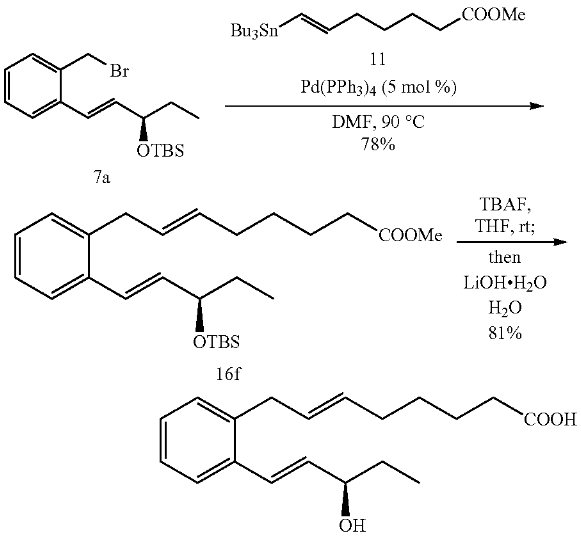

11

7a

16f 5-deoxy-o-BZ-RvE2

Methyl (E)-8-(2-((R,E)-3-((tert-butyldimethylsilyl)oxy)pent-1-en-1-yl)phenyl)oct-6-enoate (16f)

A compound (16f) (67 mg, 0.155 mmol, 78%) was synthesized from the compound (7a) (74 mg, 0.2 mmol) and the compound (11) in the same manner as the compound (9a). The analysis results of the compound (16f) were as follows.

[α]$^{19}_{D}$+22.2 (c 1.00, $CHCl_3$);

$^1H$ NMR (400 MHz, $CDCl_3$) δ 7.43 (m, 1H), 7.20-7.12 (m, 3H), 6.73 (d, J=16.0 Hz, 1H), 6.04 (dd, J=16.0, 6.4 Hz, 1H), 5.56 (dt, J=15.6, 6.4 Hz, 1H), 5.37 (dt, J=15.6, 6.8 Hz, 1H), 4.21 (ddd, J=6.4, 6.4, 6.4 Hz, 1H), 3.66 (s, 3H), 3.37 (d, J=5.6 Hz, 2H), 2.29 (t, J=7.6 Hz, 2H), 2.01 (dt, J=6.8, 6.8 Hz, 2H), 1.65-1.56 (m, 2H), 1.50-1.25 (m, 4H), 0.95-0.86 (m, 12H), 0.09 (s, 3H), 0.06 (s, 3H);

$^{13}C$ NMR (100 MHz, $CDCl_3$) δ 174.3, 138.1, 136.3, 135.1, 131.3, 129.6, 128.9, 127.5, 126.7, 126.5, 126.2, 77.4, 75.0, 51.6, 36.5, 34.1, 32.3, 31.4, 29.0, 26.1, 24.7, 18.4, 9.8, −4.1, −4.6;

LRMS (ESI) m/z 453.20 [$(M+Na)^+$];

HRMS (ESI) calcd for $C_{26}H_{42}NaO_3Si$: 453.2801 [$(M+Na)^+$], found: 458.2809.

5-Deoxy-o-BZ-RvE2

In an argon atmosphere, tetrabutylammonium fluoride (a 1 M THF solution, 276 μL, 0.276 mol, 6 eq.) was added to a THF solution (92 μL) of the compound (16f) (20 mg, 0.046 mmol), and stirring was carried out at room temperature for 24 hours. Next, an aqueous solution (92 μL) of lithium hydroxide monohydrate (8 mg, 0.184 mmol, 4 eq.) was added to the reaction solution, and stirring was carried out at room temperature for 1 hour. Then, a phosphate buffer solution (pH 6) was added thereto, and extraction was carried out with ethyl acetate. The organic layer was washed with a saturated saline solution and dried with anhydrous sodium sulfate. The solvent was distilled off under reduced pressure, the residue was purified by flash silica gel chromatography (chloroform:methanol=30:1) to obtain 5-deoxy-o-BZ-RvE2 (11.2 mg, 0.037 μmol, 81%) as a colorless oily substance. The analysis results of 5-deoxy-o-BZ-RvE2 were as follows.

$[\alpha]^{19}_{D}$−5.39 (c 0.56, MeOH);

$^{1}H$ NMR (400 MHz, $CD_3OD$) δ 7.45 (m, 1H), 7.18-7.10 (m, 3H), 6.82 (d, J=15.2 Hz, 1H), 6.06 (dd, J=15.6, 6.4 Hz, 1H), 5.57 (dt, J=15.2, 6.4 Hz, 1H), 5.37 (dt, J=15.2, 6.8 Hz, 1H), 4.13 (dt, J=6.4, 6.4 Hz, 1H), 3.38 (d, J=4.8 Hz, 2H), 2.26 (t, J=7.6 Hz, 2H), 2.02 (dt, J=6.8, 6.8 Hz, 2H), 1.71-1.54 (m, 4H), 1.38 (m, 2H), 0.97 (t, J=7.2 Hz, 3H);

$^{13}C$ NMR (100 MHz, $CD_3OD$) δ 177.8, 139.2, 137.3, 135.1, 132.3, 130.7, 128.9, 128.6, 127.4, 127.0, 75.2, 37.3, 34.9, 33.2, 31.3, 30.0, 25.6, 10.3;

LRMS (ESI) m/z 300.95 [$(M-Na)^-$];

HRMS (ESI) calcd for $C_{19}H_{25}O_3$: 301.1804 [$(M-H)^-$], found: 301.1794;

HPLC purity 98% (COSMOSIL 38020-41, $CH_3CN/H_2O$/TFA=50/50/0.01, 1.0 mL/min, $t_R$=13.9 min, detection at 254 nm).

<Anti-Inflammatory Property Evaluation Assay>

300 pg of RvE2, o-BZ-RvE2, 17-deoxy-o-BZ-RvE2, 5-deoxy-o-BZ-RvE2, or 5,17-dideoxy-o-BZ-RvE2, or only a solvent was intraperitoneally administered to acute inflammation model mice 8 hours after the injection of *Propionibacterium acnes* (n=3 or 4). Then, 24 hours after the injection of *Propionibacterium acnes*, a peritoneal exudate was collected and the number of neutrophils was counted. The results are shown in FIG. 3.

Figure 3:
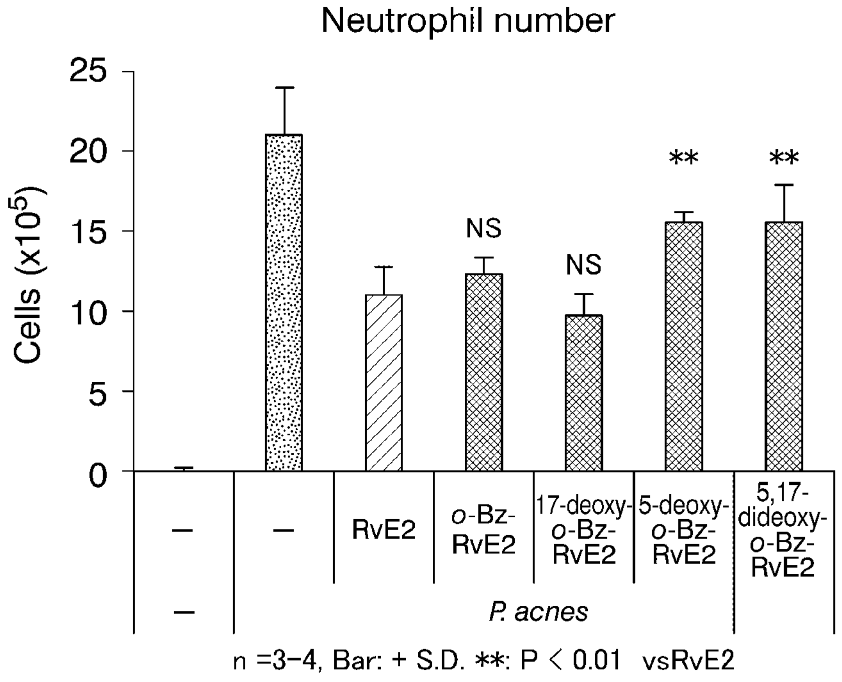
FIG. 3 is a graph showing the results of carrying out anti-inflammatory property evaluation assays of RvE2, o-BZ-RvE2, 17-deoxy-o-BZ-RvE2, 5-deoxy-o-BZ-RvE2, and 5,17-dideoxy-o-BZ-RvE2 in Example 2.

As shown in FIG. 3, in the mice inoculated with *Propionibacterium acnes* as a control, the number of neutrophils was significantly increased as compared with the untreated group (leftmost column in the figure), whereas in the mice treated with RvE2, o-BZ-RvE2, 17-deoxy-o-BZ-RvE2, 5-deoxy-o-BZ-RvE2, and 5,17-dideoxy-o-BZ-RvE2, the number of neutrophils was significantly decreased. In particular, in the group administered with 17-deoxy-BZ-RvE2, the number of neutrophils was decreased to the same extent as the group administered with RvE2 and the group administered with o-BZ-RvE2, and the high anti-inflammatory activity was maintained. On the other hand, in the group administered with 5-deoxy-BZ-RvE2 and the group administered with 5,17-dideoxy-BZ-RvE2, the anti-inflammatory activity was attenuated as compared with the group administered with RvE2 or o-BZ-RvE2. These results suggest that the hydroxyl group present at the 6 position of a carboxylic acid is important for the expression of the anti-inflammatory activity of o-BZ-RvE2.

<Evaluation of Metabolic Stability>

The metabolic stability of 17-deoxy-o-BZ-RvE2 and 5-deoxy-o-BZ-RvE2 with respect to human liver microsomes was investigated. Specifically, for RvE2, o-BZ-RvE2, 17-deoxy-o-BZ-RvE2, and 5-deoxy-o-BZ-RvE2, the temporal change in the remaining rate (%) was measured by HPLC in 0.1 M PBS (pH 7.4) in the presence of human liver microsomes at 37 °C (n=3). The results are shown in FIG. 4.

Figure 4:
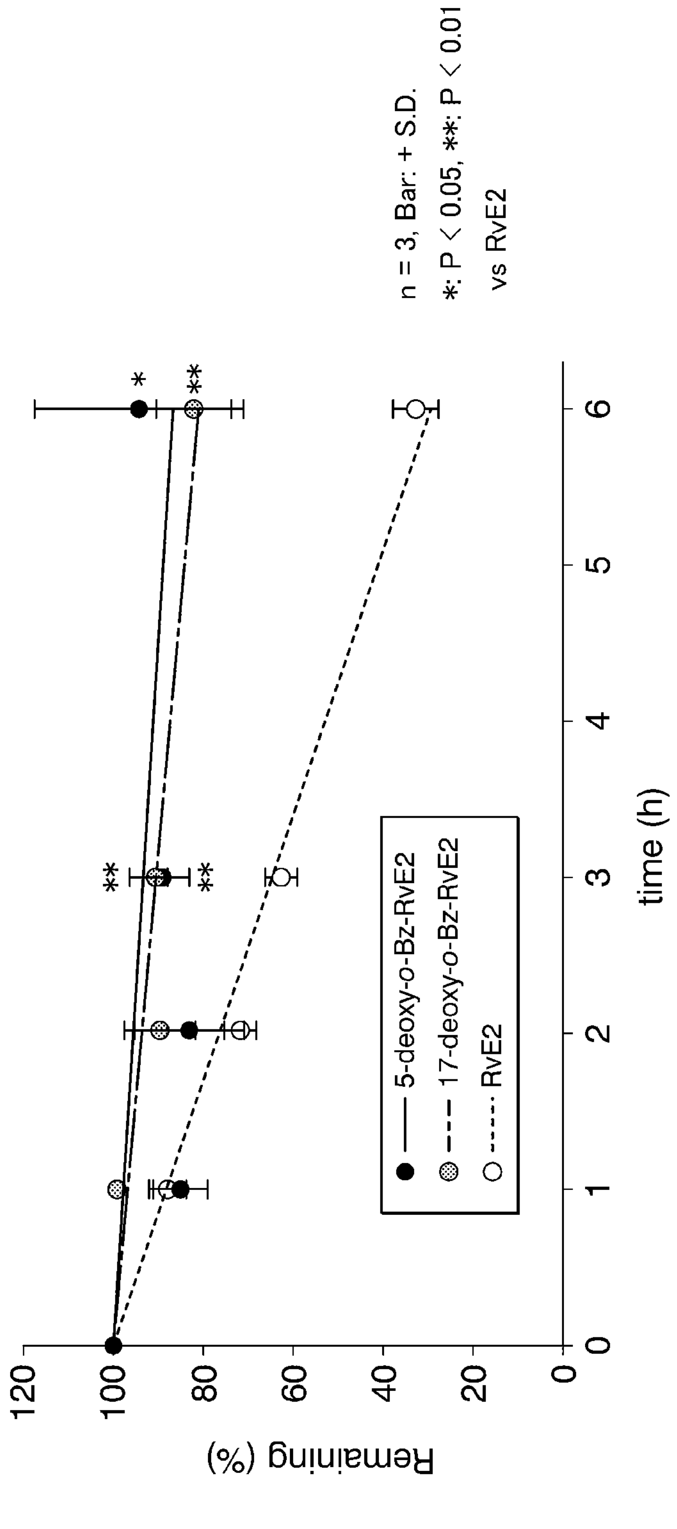
FIG. 4 is a graph showing the results of carrying out metabolic stability evaluation assays of RvE2, o-BZ-RvE2, 17-deoxy-o-BZ-RvE2, and 5-deoxy-o-BZ-RvE2 with respect to human liver microsomes in Example 2.

As shown in FIG. 4, the remaining rate of RvE2 decreased with the passage of time, whereas the remaining rate of 5-deoxy-BZ-RvE2 and 17-deoxy-BZ-RvE2 gradually decreased as compared with RvE2, which showed that the metabolic stability is high. In addition, since there was no significant difference in the metabolic stability between both deoxy derivatives, it was conceived that the attenuation of the anti-inflammatory activity in 5-deoxy-o-BZ-RvE2 was not due to metabolic resistance.

Example 3

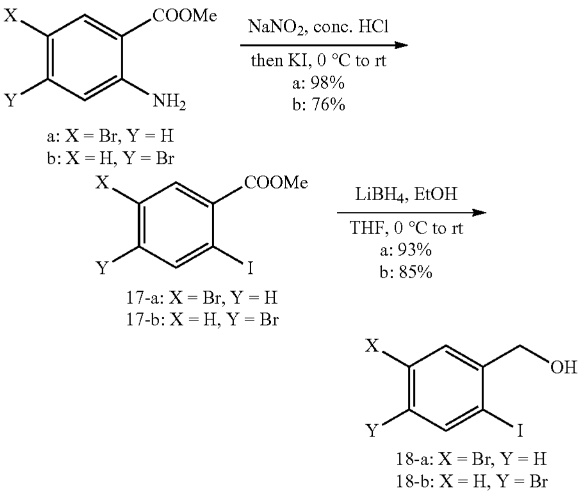

Methyl 5-bromo-2-iodobenzotate (17-a)

In an argon atmosphere, methyl 5-bromoanthranilate (200 mg, 0.869 mmol) was dissolved in hydrochloric acid (12 M, 2.1 mL), and stirring was carried out at 0 °C After 15 minutes, ice (1.0 g) was added, and stirring was carried out at 0 °C After 10 minutes, a solution obtained by dissolving sodium nitrite (120 mg, 3.82 mmol, 2.0 eq.) in water (1.5 mL) was added, and stirring was carried out at 0 °C After 10 minutes, a solution obtained by dissolving potassium iodide (634 mg, 3.82 mmol, 4.4 eq.) in water (2.9 mL) was added, and stirring was carried out at room temperature. After 1 hour, a saturated aqueous solution of sodium thiosulfate solution was added to the reaction solution to stop the reaction, and extraction was carried out with ethyl acetate. The organic layer was washed with a saturated saline solution, dried with a Glauber's salt, and the solvent was distilled off under reduced pressure. The purification was carried out by silica gel chromatography (hexane:ethyl acetate=9:1) to obtain a compound (17-a) (283 mg, 0.831 mmol, 96%) as yellow crystals.

$^1$H NMR (400 MHz, $CDCl_3$) δ 7.94 (d, J=2.0 Hz, 1H), 7.84 (d, J=8.4, 1H), 7.28 (dd, J=8.4, 2.0 Hz, 1H), 3.94 (s, 3H); the spectral data from other various instruments were compared with the data described in Non-Patent Document 4 to carry out identification. However, the synthesis method is different from that of Non-Patent Document 4.

Methyl 4-bromo-2-iodobenzoate (17-b)

A compound (17-b) (226 mg, 0.66 mmol, 76%) was synthesized from methyl 4-bromoanthranilate (200 mg, 0.869 mmol) in the same manner as the compound (17-a).

$^1$H NMR (400 MHz, $CDCl_3$) δ 8.18 (d, J=2.0 Hz, 1H), 7.70 (d, J=8.4, 1H), 7.54 (dd, J=8.4, 2.0 Hz, 1H), 3.93 (s, 3H); the spectral data from other various instruments were compared with the data described in Non-Patent Document 5 to carry out identification. However, the synthesis method is different from that of Non-Patent Document 5.

(5-Bromo-2-iodophenyl)methanol (18-a)

In an argon atmosphere, ethanol (5.4 mL, 92 mmol, 4.0 eq.) and $LiBH_4$ (1.00 g, 46 mmol, 2.0 eq.) were added to a solution obtained by dissolving the compound (17-a) (7.93 g, 23.0 mmol) in THF (46 mL) under ice cooling, and stirring was carried out for 1 hour. Further, the temperature was raised to room temperature, and stirring was carried out for 12 hours. A saturated aqueous solution of ammonium chloride was added to the reaction solution to stop the reaction, and extraction was carried out with ethyl acetate. The obtained organic layer was washed with a saturated saline solution, anhydrous sodium sulfate was added thereto, and dried. The solvent was distilled off under reduced pressure, and the residue was purified by silica gel chromatography (hexane:ethyl acetate=4:1) to obtain a compound (18-a) (6.67 g, 21.3 mmol, 93%) as a white powdery substance.

$^1$H NMR (400 MHz, $CDCl_3$) δ 7.65 (d, J=8.4 Hz 1H), 7.63 (d, J=2.4 Hz, 1H), 7.14 (dd, J=8.4, 2.4 Hz, 1H), 4.64 (d, J=6.4 Hz, 2H), 2.00 (t, J=6.4 Hz, 1H); the spectral data from other various instruments were compared with the data described in Non-Patent Document 4 to carry out identification. However, the synthesis method is different from that of Non-Patent Document 4.

(4-Bromo-2-iodophenyl)methanol (18-b)

A compound (18-b) (5.45 g, 17.4 mmol, 85%) was synthesized from the compound (17-b) (6.97 g, 20.4 mmol) in the same manner as the compound (18-a).

$^1$H NMR (400 MHz, $CDCl_3$) δ 7.97 (d, J=2.0 Hz 1H), 7.51 (dd, J=8.0, 2.0 Hz, 1H), 7.34 (d, J=8.0 Hz, 1H), 4.63 (d, J=6.4 Hz, 2H), 1.94 (t, J=6.4 Hz, 1H); $^{13}$C NMR (100 MHz, $CDCl_3$) δ 141.6, 140.9, 131.5, 129.3, 121.7, 97.4, 68.6.

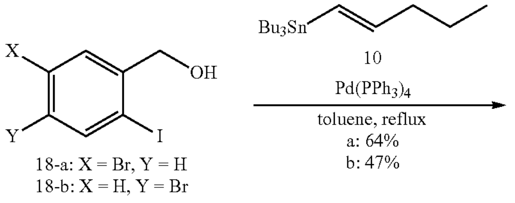

-continued

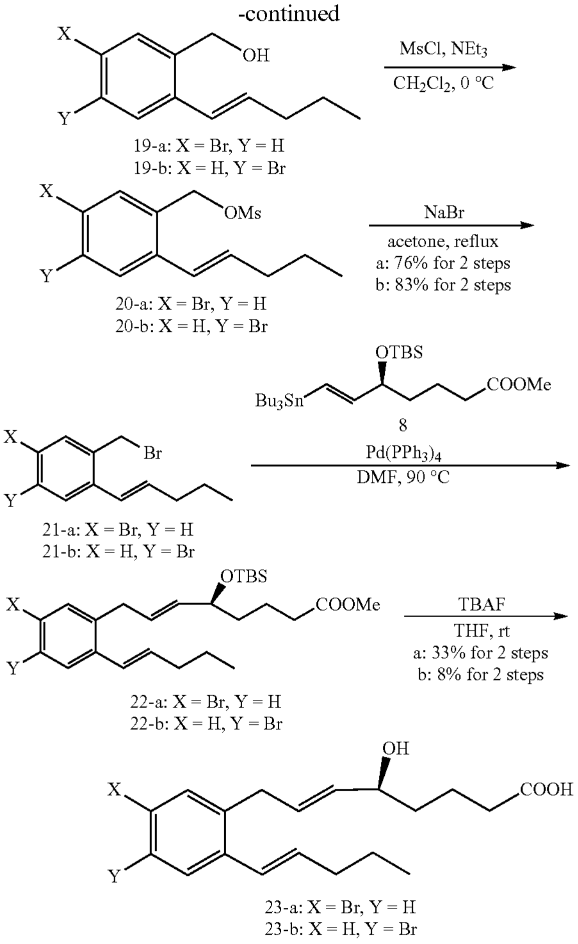

(E)-(5-bromo-2-(pent-1-en-1-yl)phenyl)methanol (19-a)

In an argon atmosphere, the compound (18-a) (250 mg, 0.80 mmol) and the compound (10) (287 mg, 0.80 mmol, 1.0 eq.) were dissolved in toluene (5.5 mL), tetrakistriphenylphosphine palladium (46 mg, 0.04 mmol, 0.05 eq.) was added thereto, and stirring was carried out for 24 hours under heating and reflux. A saturated aqueous solution of ammonium chloride was added to the reaction solution to stop the reaction, and extraction was carried out with ethyl acetate. The obtained organic layer was washed with a saturated saline solution, anhydrous sodium sulfate was added thereto, and dried. The solvent was distilled off under reduced pressure, and the residue was purified by silica gel chromatography (10% w/w $K_2CO_3$—SiOH, hexane:ethyl acetate=19:1 to 9:1) to obtain a compound(19-a) (130 mg, 0.51 mmol, 64%) as a yellow oily substance.

$^1$H NMR (400 MHz, $CDCl_3$) δ 7.58 (d, J=2.0 Hz, 1H), 7.37 (dd, J=8.6, 2.0 Hz, 1H), 7.31 (d, J=8.6 Hz, 1H), 6.54 (d, J=16.0 Hz, 1H), 6.14 (dt, J=16.0, 7.2 Hz, 1H), 4.71 (d, J=6.0 Hz, 2H), 2.20 (dt, J=7.2, 7.2 Hz, 2H), 1.70 (m, 1H), 1.50 (tq, J=7.6, 7.2 Hz, 2H), 0.96 (t, J=7.6 Hz, 3H); $^{13}$C NMR (100 MHz, $CDCl_3$) δ 140.3, 139.0, 135.5, 134.6, 130.8, 130.6, 127.6, 125.5, 62.8, 35.4, 22.4, 13.7.

(E)-(4-bromo-2-(pent-1-en-1-yl)phenyl)methanol (19-b)

A compound (19-b) (22 mg, 0.084 mmol, 47%) was synthesized from the compound (18-b) (56 mg, 0.178 mmol)

and the compound (10) (64 mg, 0.178 mmol, 1.0 eq.) in the same manner as the compound (19-a).

$^1H$ NMR (400 MHz, $CDCl_3$) δ 7.59 (d, J=2.0 Hz, 1H), 7.34 (dd, J=8.8, 2.0 Hz, 1H), 7.22 (d, J=8.8 Hz, 1H), 6.59 (d, J=16.0 Hz, 1H), 6.17 (dt, J=16.0, 7.2 Hz, 1H), 4.69 (d, J=6.0 Hz, 2H), 2.22 (dt, J=7.2, 6.8 Hz, 2H), 1.26 (m, 1H), 1.57-1.46 (m, 2H), 0.96 (t, J=7.6 Hz, 3H); $^{13}C$ NMR (100 MHz, $CDCl_3$) δ 138.8, 135.9, 135.3, 129.7, 129.7, 128.9, 125.3, 122.0, 62.9, 35.3, 22.4, 13.7.

(E)-4-bromo-2-(bromomethyl)-1-(pent-1-en-1-yl) benzene (21-a)

In an argon atmosphere, triethylamine (31 μL, 0.22 mmol, 1.1 eq.) and methanesulfonyl chloride (17 μL, 0.22 mmol, 1.1 eq.) were added at 0 °C to a solution obtained by dissolving the compound (19-a) (50 mg, 0.20 mmol) in dichloromethane (2.0 mL), and stirring was carried out. After 90 minutes, a saturated saline solution was added thereto, thereby being quenched, and extraction was carried out with ethyl acetate. Anhydrous sodium sulfate was added to the obtained organic layer and dried. The solvent was distilled off under reduced pressure to obtain a compound 20-a as a crude product. The crude product was dissolved in acetone (2.0 mL), sodium bromide (112 mg, 1.09 mmol, 6.0 eq.) was added, and reflux was carried out for 12 hours. A saturated saline solution was added to the reaction solution, and extraction was carried out with ethyl acetate. The solvent was distilled off under reduced pressure, and the residue was purified by silica gel chromatography (hexane: ethyl acetate=9:1) to obtain a compound (21-a) (48.5 mg, 0.152 mmol, 76% for 2 steps) as a yellow oily substance.

$^1H$ NMR (400 MHz, $CDCl_3$) δ 7.43 (d, J=2.0 Hz, 1H), 7.38-7.36 (m, 1H), 7.32 (d, J=8.4 Hz, 1H), 6.62 (d, J=16.0 Hz, 1H), 6.20 (dt, J=16.0, 7.2 Hz, 1H), 4.47 (s, 2H), 2.26-2.20 (m, 2H), 1.56-1.50 (m, 2H), 0.97 (t, J=7.2 Hz, 3H); $^{13}C$ NMR (100 MHz, $CDCl_3$) δ 136.5, 135.8, 135.2, 132.8, 132.0, 128.1, 125.3, 120.4, 35.4, 30.7, 22.3, 13.7.

(E)-4-bromo-1-(bromomethyl)-2-(pent-1-en-1-yl) benzene (21-b)

A compound (21-b) (16 mg, 0.052 mmol, 83% for 2 steps) was synthesized from the compound (19-b) (16 mg, 0.062 mmol) in the same manner as the compound (21-a).

$^1H$ NMR (400 MHz, $CDCl_3$) δ 7.58 (d, J=2.0 Hz, 1H), 7.30 (dd, J=8.4, 2.0 Hz, 1H), 7.15 (d, J=8.4 Hz, 1H), 6.63 (d, J=15.6 Hz, 1H), 6.22 (dt, J=15.6, 7.2 Hz, 1H), 4.84 (s, 2H), 2.27-2.22 (m, 2H), 1.26 (tq, J=7.6, 7.2 Hz, 2H), 0.96 (t, J=7.6 Hz, 3H); $^{13}C$ NMR (100 MHz, $CDCl_3$) δ 139.5, 135.9, 133.0, 131.6, 130.1, 129.5, 125.1, 123.1, 35.4, 31.0, 22.3, 13.7.

(S,E)-8-(5-bromo-2-((E)-pent-1-en-1-yl)phenyl)-5-hydroxyoct-6-enoic Acid (23-a)

In an argon atmosphere, the compound (21-a) (24.3 mg, 43.3 μmol, 1.5 eq.) and the compound (8) (9.2 mg, 28.8 μmol, 1.0 eq.) were dissolved in dimethylformamide (1.0 mL), tetrakistriphenylphosphine palladium (2.1 mg, 1.81 μmol, 0.05 eq.) was added thereto, and stirring was carried out for 18 hours under heating and reflux. A saturated saline solution was added to the reaction solution to stop the reaction, and extraction was carried out with ethyl acetate. The obtained organic layer was washed with a saturated saline solution, anhydrous sodium sulfate was added thereto, and dried. The solvent was distilled off under reduced pressure, and the residue was purified by flash silica gel chromatography (hexane:ethyl acetate=99:1), and an obtained compound (22-a) was used as it was in the next reaction. The compound (22-a) was dissolved in tetrahydrofuran (100 μL), tetrabutylammonium fluoride (a 1 M THF solution, 107 μL, 107 μmol, 4 eq.) was added thereto, and stirring was carried out at room temperature for 2 days. A phosphate buffer (pH 6) was added to the reaction solution, and extraction was carried out with ethyl acetate. The organic layer was washed with a saturated saline solution and dried with anhydrous sodium sulfate. The solvent was distilled off under reduced pressure and purified by silica gel chromatography (chloroform:methanol=30:1) to obtain a compound (23-a) (3.6 mg, 9.43 μmol, 33% for 2 steps) as a colorless oily substance.

$^1H$ NMR (400 MHz, $CDCl_3$) δ 7.29 (m, 2H), 7.24 (m, 1H), 6.47 (d, J=16.0 Hz, 1H), 6.08 (dt, J=16.0, 7.2 Hz, 1H), 5.77 (m, 1H), 5.45 (dd, J=15.6, 6.8 Hz, 1H), 4.11 (m, 1H), 3.37 (d, J=6.0 Hz, 2H), 2.40 (t, J=6.8 Hz, 2H), 2.35-2.17 (m, 2H), 2.06-1.44 (m, 7H), 0.95 (t, J=7.6 Hz, 3H)

(S,E)-8-(4-bromo-2-((E)-pent-1-en-1-yl)phenyl)-5-hydroxyoct-6-enoic Acid (23-b)

A compound (23-b) (1.8 mg, 4.72 mmol, 8% for 2 steps) was synthesized from the compound (21-b) (52.6 mg, 93.7 μmol, 1.5 eq.) and the compound (8) (20 mg, 62.9 μmol, 1.0 eq.) in the same manner as the compound (23-a).

$^1H$ NMR (400 MHz, $CDCl_3$) δ 7.25 (m, 1H), 6.98 (m, 2H), 6.47 (d, J=16.0 Hz, 1H), 6.33 (m, 1H) 5.65 (m, 1H), 5.33 (dd, J=15.6, 6.4 Hz, 1H), 4.06 (m, 1H), 3.37 (d, J=6.0 Hz, 2H), 2.29 (t, J=7.6 Hz, 2H), 2.18 (m, 2H), 1.69-1.46 (m, 7H), 0.95 (t, J=7.6 Hz, 3H)

What is claimed is:

1. A compound represented by the following General Formula (1-o-1), (1-o-2), (1-m-1), or (1-m-2), (1-o-1)

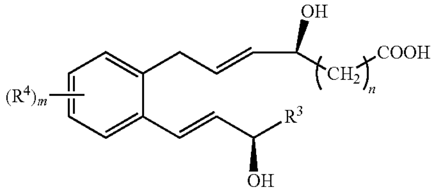

(1-o-2)

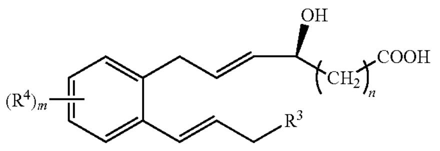

(1-m-1)

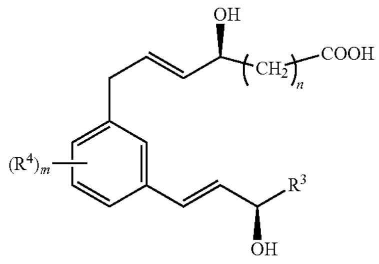

-continued (1-m-2)

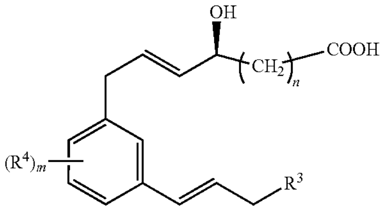

where $R^3$ represents an alkyl group having 1 to 6 carbon atoms; $R^4$ represents a halogen atom or an alkyl group; m indicates the number of $R^4$ and represents an integer of 0 to 4; in a case where m is 2 or more, a plurality of $R^4$'s may be the same or different from each other; and n represents an integer of 1 to 6.

2. The compound according to claim 1, wherein the halogen atom is a fluorine atom, a chlorine atom, a bromine atom, or an iodine atom, and the alkyl group is a methyl group.

3. The compound according to claim 1, wherein the halogen atom is a bromine atom.

4. The compound according to claim 1, wherein in General Formula (1-o-1), (1-o-2), (1-m-1), or (1-m-2), $R^4$ represents 0 or 1.

5. The compound according to claim 1, wherein in General Formula (1-o-1), (1-o-2), (1-m-1), or (1-m-2), $R^4$ is substituted at a meta-position or a para-position of a substituent having a carboxylic acid group.

6. The compound according to claim 1, wherein the compound is represented by the General Formula (1-o-1), (1-o-2), (1-m-1), or (1-m-2), and m represents 0.

7. The compound according to claim 1, wherein the compound is represented by the General Formula (1-o-1) or (1-o-2), and m represents 0.

8. The compound according to claim 1, wherein the compound is represented by the following General Formula (1-o-1-1):

(1-o-1-1)

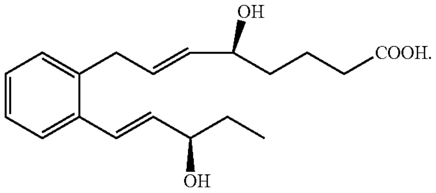

9. The compound according to claim 1, wherein the compound is represented by the following General Formula (1-o-2-1):

(1-o-2-1)

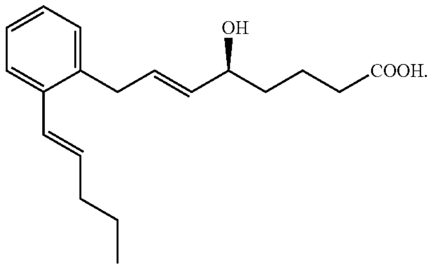

10. A neutrophil infiltration suppressor comprising, as an active ingredient:

the compound according to claim 1.

11. An anti-inflammatory agent comprising, as an active ingredient:

the compound according to claim 1.

12. An antidepressant comprising, as an active ingredient:

the compound according to claim 1.

13. A pharmaceutical composition comprising, as an active ingredient:

the compound according to claim 1.

14. The pharmaceutical composition according to claim 13, wherein the pharmaceutical composition is used for treating inflammation.

15. The pharmaceutical composition according to claim 13, wherein the pharmaceutical composition is used for treating depression.

* * * * *